(12) United States Patent
Shulman et al.

(10) Patent No.: US 9,732,333 B2
(45) Date of Patent: Aug. 15, 2017

(54) NUCLEIC ACID CONSTRUCT FOR EXPRESSION OF ALPHA-GALACTOSIDASE IN PLANTS AND PLANT CELLS

(75) Inventors: Avidor Shulman, Rakefet (IL); Uri Hanania, Carmiel (IL); Tali Kizhner, Yishuv Atzmon-Segev (IL); Yoseph Shaaltiel, Kibbutz HaSolelim (IL)

(73) Assignee: Protalix Ltd., Carmiel (IL)

( * ) Notice: Subject to any disclaimer, the term of this patent is extended or adjusted under 35 U.S.C. 154(b) by 781 days.

(21) Appl. No.: 13/980,910

(22) PCT Filed: Sep. 7, 2011

(86) PCT No.: PCT/IL2011/000719
§ 371 (c)(1),
(2), (4) Date: Jul. 22, 2013

(87) PCT Pub. No.: WO2012/098537
PCT Pub. Date: Jul. 26, 2012

(65) Prior Publication Data
US 2013/0295065 A1    Nov. 7, 2013

Related U.S. Application Data

(63) Continuation-in-part of application No. PCT/IL2011/000209, filed on Mar. 2, 2011.

(60) Provisional application No. 61/434,499, filed on Jan. 20, 2011, provisional application No. 61/434,503, filed on Jan. 20, 2011.

(51) Int. Cl.
| | | |
|---|---|---|
| *C12N 9/40* | (2006.01) | |
| *C12N 15/12* | (2006.01) | |
| *A61K 38/16* | (2006.01) | |
| *A61K 38/47* | (2006.01) | |
| *C12N 15/82* | (2006.01) | |

(52) U.S. Cl.
CPC .......... *C12N 9/2465* (2013.01); *A61K 38/47* (2013.01); *C12N 15/8257* (2013.01)

(58) Field of Classification Search
None
See application file for complete search history.

(56) References Cited

U.S. PATENT DOCUMENTS

| | | | |
|---|---|---|---|
| 5,580,757 A | 12/1996 | Desnick et al. | |
| 5,595,756 A | 1/1997 | Bally et al. | |
| 5,614,587 A | 3/1997 | Rhee et al. | |
| 5,766,897 A | 6/1998 | Braxton | |
| 5,994,086 A | 11/1999 | Benoff | |
| 6,309,646 B1 | 10/2001 | Lees | |
| 6,395,884 B1 | 5/2002 | Selden et al. | |
| 6,846,968 B1 | 1/2005 | Erwin et al. | |
| 7,011,831 B2 | 3/2006 | Calhoun et al. | |
| 8,426,357 B2 | 4/2013 | Kraehmer et al. | |
| 2002/0088024 A1* | 7/2002 | Garger .................. C07K 14/005 | 800/284 |
| 2002/0137125 A1 | 9/2002 | Zhu | |
| 2003/0190304 A1 | 10/2003 | Thompson et al. | |
| 2003/0228612 A1* | 12/2003 | Kenward ........... C12N 15/8257 | 435/6.13 |
| 2005/0048047 A1 | 3/2005 | Kakkis | |
| 2005/0058634 A1 | 3/2005 | Zhu | |
| 2005/0059097 A1 | 3/2005 | Daunert et al. | |
| 2005/0180948 A1 | 8/2005 | Desjarlais et al. | |
| 2005/0282225 A1 | 12/2005 | Daunert et al. | |
| 2006/0084163 A1 | 4/2006 | Schaffer et al. | |
| 2006/0204487 A1 | 9/2006 | Shaaltiel et al. | |
| 2006/0228348 A1 | 10/2006 | Stefano | |
| 2007/0172449 A1 | 7/2007 | Carmichael et al. | |
| 2007/0207961 A1 | 9/2007 | Dahiyat et al. | |
| 2012/0230974 A1 | 9/2012 | Shaaltiel et al. | |
| 2012/0328589 A1 | 12/2012 | Ruderfer et al. | |
| 2012/0328592 A1 | 12/2012 | Shulman et al. | |
| 2013/0017169 A1 | 1/2013 | Ruderfer et al. | |

FOREIGN PATENT DOCUMENTS

| | | |
|---|---|---|
| EP | 0747066 | 12/1996 |
| GB | 2402677 | 12/2004 |
| JP | 2005-043317 | 2/2005 |
| KR | 20070065157 | 6/2007 |
| WO | WO 91/14697 | 10/1991 |
| WO | WO 93/18148 | 9/1993 |
| WO | WO 95/01994 | 1/1995 |
| WO | WO 95/06478 | 3/1995 |
| WO | WO 96/23869 | 8/1996 |
| WO | WO 97/10353 | 3/1997 |
| WO | WO 98/13469 | 4/1998 |
| WO | WO 01/25277 | 4/2001 |
| WO | WO 02/057435 | 7/2002 |
| WO | WO 03/035686 | 5/2003 |

(Continued)

OTHER PUBLICATIONS

Napier (Journal of Experimental Biology, 1995, 46(293): 1787-1795).*
GenBank S31584 (see office action).*
GenBank AY093754 (see office action).*
Terrier et al. (Biotechnol. Bioeng. 2007, 96: 914-923).*
Rade et al (Gene Therapy, 1999, 6:385-392).*
Official Action Dated May 8, 2014 From the US Patent and Trademark Office Re. U.S. Appl. No. 13/582,482.
Sen et al. "Developments in Directed Evolution for Improving Enzyme Functions", Applied Biochemistry and Biotechnology, 143: 212-223, Aug. 18, 2007.
Shaaltiel et al. "Alpha-Gal-KDEL Construct DNA Encoding Protein Seq ID:20", Score Database [Online], Database Accession No. ATS59772, Jan. 8, 2009.
Shaaltiel et al. "Human Recombinant Alpha Galactosidase a 47.6 kDa Protein", Score Database [Online], Database Accession No. ATS59778, Jan. 8, 2009.
Huang et al. "Research Advances in Auxin-Binding Proteins", Journal of Anhui Agricultural Sciences, 35(29): 9119-9120, 2007. Abstract in English.

(Continued)

*Primary Examiner* — John S Brusca
*Assistant Examiner* — Stephen Uyeno

(57) ABSTRACT

Nucleic acid expression constructs are provided and, more particularly, nucleic acid constructs for expression of human alpha-galactosidase in plant cells, cells expressing the nucleic acid construct, producing the human alpha-galactosidase and uses thereof.

24 Claims, 8 Drawing Sheets
(1 of 8 Drawing Sheet(s) Filed in Color)

(56) References Cited

FOREIGN PATENT DOCUMENTS

| WO | WO 03/042244 | 5/2003 |
|----|----|----|
| WO | WO 03/090695 | 11/2003 |
| WO | WO 03/097791 | 11/2003 |
| WO | WO 2004/081053 | 9/2004 |
| WO | WO 2004/091475 | 10/2004 |
| WO | WO 2004/096978 | 11/2004 |
| WO | WO 2004/111198 | 12/2004 |
| WO | WO 2005/056760 | 6/2005 |
| WO | WO 2005/077093 | 8/2005 |
| WO | WO 2005/093422 | 10/2005 |
| WO | WO 2006/093524 | 9/2006 |
| WO | WO 2006/108052 | 10/2006 |
| WO | WO 2007/010533 | 1/2007 |
| WO | WO 2008/012540 | 1/2008 |
| WO | WO 2008/075957 | 6/2008 |
| WO | WO 2008/089403 | 7/2008 |
| WO | WO 2008/132743 | 11/2008 |
| WO | WO 2009/024977 | 2/2009 |
| WO | WO 2010/004568 | 1/2010 |
| WO | WO 2011/107992 | 9/2011 |
| WO | WO 2012/098537 | 7/2012 |

OTHER PUBLICATIONS

Advisory Action Before the Filing of an Appeal Brief Dated Mar. 5, 2013 From the US Patent and Trademark Office Re. U.S. Appl. No. 12/673,987.
Communication Pursuant to Article 94(3) EPC Dated Oct. 7, 2010 From the European Patent Office Re. Application No. 08789815.1.
Communication Relating to the Results of the Partial International Search Dated Sep. 18, 2009 From the International Searching Authority Re.: Application No. PCT/IL2008/001143.
Communication Relating to the Results to the Partial International Search Dated Jul. 4, 2011 From the International Searching Authority Re. Application No. PCT/IL2011/000211.
Examination Report Dated Apr. 10, 2013 From the Intellectual Property Office of New Zealand Re. Application No. 602317.
Examination Report Dated Feb. 28, 2013 From the Australian Government, IP Australia Re. Application No. 2008290217.
International Preliminary Report on Patentability Dated Mar. 4, 2010 From the International Bureau of WIPO Re.: Application No. PCT/IL2008/001143.
International Preliminary Report on Patentability Dated Sep. 13, 2012 From the International Bureau of WIPO Re. Application No. PCT/IL2011/000209.
International Preliminary Report on Patentability Dated Sep. 13, 2012 From the International Bureau of WIPO Re. Application No. PCT/IL2011/000210.
International Preliminary Report on Patentability Dated Sep. 13, 2012 From the International Bureau of WIPO Re. Application No. PCT/IL2011/000211.
International Preliminary Report on Patentability Dated May 31, 2012 From the International Bureau of WIPO Re. Application No. PCT/IL2010/000956.
International Search Report and the Written Opinion Dated Feb. 2, 2012 From the International Searching Authority Re. Application No. PCT/IL2011/000719.
International Search Report and the Written Opinion Dated Mar. 14, 2011 From the International Searching Authority Re. Application No. PCT/IL2010/000956.
International Search Report and the Written Opinion Dated Jun. 22, 2011 From the International Searching Authority Re. Application No. PCT/IL2011/000210.
International Search Report and the Written Opinion Dated Nov. 23, 2009 From the International Searching Authority Re.: Application No. PCT/IL2008/001143.
International Search Report and the Written Opinion Dated Jun. 24, 2011 From the International Searching Authority Re. Application No. PCT/IL2011/000209.
International Search Report and the Written Opinion Dated Sep. 28, 2011 From the International Searching Authority Re. Application No. PCT/IL2011/000211.
Office Action Dated Mar. 11, 2013 From the Israel Patent Office Re. Application No. 204037 and Its Translation Into English.
Official Action Dated Jul. 1, 2013 From the US Patent and Trademark Office Re. U.S. Appl. No. 12/673,987.
Official Action Dated Jul. 16, 2012 From the US Patent and Trademark Office Re. U.S. Appl. No. 12/673,987.
Official Action Dated Nov. 28, 2012 From the US Patent and Trademark Office Re. U.S. Appl. No. 12/673,987.
Response Dated Feb. 3, 2011 to Communication Pursuant to Article 94(3) EPC of Oct. 7, 2010 From the European Patent Office Re. Application No. 08789815.1.
Restriction Official Action Dated Apr. 12, 2013 From the US Patent and Trademark Office Re. U.S. Appl. No. 13/582,464.
Restriction Official Action Dated Apr. 17, 2012 From the US Patent and Trademark Office Re. U.S. Appl. No. 12/673,987.
Restriction Official Action Dated Feb. 28, 2013 From the US Patent and Trademark Office Re. U.S. Appl. No. 13/510,340.
Bendele et al. "Short Communication: Renal Tubular Vacuolation in Animals Treated With Polyethylene-Glycol-Conjugated Proteins", Toxicological Sciences, 42: 152-157, 1998.
Benoff et al. "Use of Mannose Ligands in IVF Screens to Mimic Zona Pellucida-Induced Acrosome Reactions and Predict Fertilization Success", Molecular Human Reproduction, XP002554818, 3(10): 839-846, Oct. 1997. Abstract.
Buckmann et al. "Synthesis of Water Soluble Polymers With Covalently Bound General Ligands", Enzyme Engineering, 4: 395-397, 1978.
Bueckmann et al. "Functionalization of Poly(Ethylene Glycol) and Monomethoxy-Poly(Ethylene Glycol)", Die Makromolekulare Chemie, 182(5): 1379-1384, May 1981.
Chen et al. "Directed Evolution of a Lysosomal Enzyme With Enhanced Activity at Neutral pH by Mammalian Cell-Surface Display", Chemistry and Biology, 15: 1277-1286, 2008.
Cramer et al. "Transgenic Plants for Therapeutic Proteins: Linking Upstream and Downstream Strategies", Current Topics in Microbiology and Immunology, XP009038354, 240(3): 95-118, 1999.
Den Dulk-Ras et al. "Electroporation of Agrobacterium Tumefaciens", Methods in Molecular Biology, 55: 63-72, 1995. Abstract.
Fernandez-Megia et al. "Conjugation of Bioactive Ligands to PEG-Grafted Chitosan at the Distal End of PEG", Biomacromolecules, XP002554819, 8(3): 833-842, Mar. 2007.
Gao et al. "A Novel Alkaline ?-Galactosidase From Melon Fruit With a Substrate Preference for Raffinose", Plant Physiology, XP002128580, 119(3): 979-987, Mar. 1, 1999. Abstract, p. 980-981: "Alkaline ?-Galactosidase Purification".
Gleba et al. "Magnifection—A New Platform for Expressing Recombinant Vaccines in Plants", Vaccine, 23: 2042-2048, 2005.
Grosse et al. "Intracellular Rate-Limiting Steps of Gene Transfer Using Glycosylated Polylysines in Cystic Fibrosis Airway Epithelial Cells", Gene Therapy, XP002554817, 9(15): 1000-1007, Aug. 2002. p. 1005, col. 1, § 4.
Hoffmann "Fabry Disease: Recent Advances in Pathology, Diagnosis, Treatment and Monitoring", Orphanet Journal of Rare Diseases, 4(21): 1-9, Oct. 11, 2009.
Kapoor "How to Cross-Link Proteins", FGSC (Fungal Genetics Stock Center), University of Missouri, MO, USA, p. 1-6, Mar. 28, 2006. Retrieved From the Internet.
Laville et al. "Photodynamic Efficiency of Diethylene-Linked Glycoconjugated Porphyrins in Human Retinoblastoma Cells", Journal of Medicinal Chemistry, XP002554822, 49(8): 2558-2567, Apr. 2006. Figs.1-3.
Li et al. "Bacteria Targeted by Human Natural Antibodies Using Alpha-Gal Conjugated Receptor-Specific Glycopolymers", Bioorganic and Medicinal Chemistry, XP002554821, 7(8): 1549-1558, Aug. 1999. Figs.1-5.
Lindhorst et al. "Trivalent Alpha-D-Mannoside Clusters as Inhibitors of Type-1 Fimbriae-Mediated Adhesion of *Escherichia Coli*:

(56) References Cited

OTHER PUBLICATIONS

Structural Variation and Biotinylation", Journal of the chemical Society, Perkin Transactions 1, XP002554820, 8: 823-831, Apr. 21, 2001.
Neumann et al. "Protein Transport in Plant Cells: In and Out of the Golgi", Annals of Botany, 92: 167-180, 2003.
Pagny et al. "Signals and Mechanisms for Protein Retention in the Endoplasmic Reticulum", Journal of Experimental Botany, 50(331): 157-164, Feb. 1999.
Potrykus "Gene Transfer to Plants: Assessment of Public Approaches and Results", Annual Review of Plant Physiology & Plant Molecular Biology, 42: 205-225, 1991.
Rathnam et al. "Conjugation of a Fetuin Glycopeptide to Human Follicle-Stimulating Hormone and Its Subunits by Photoactivation", Biochimica et Biophysica Acta, XP002554815, 624(2): 436-442, 1980. Fig.1.
Rayon et al. "The Protein N-Glycosylation in Plants", Journal of Experimental Botany, 49(326): 1463-1472, Sep. 1998.
Schottelius et al. "Detection and Quantitation of Cell-Surface Sugar Receptor(s) of Leishmania Donovani by Application of Neoglycoenzymes", Parasitology Research, XP008114350, 78(6): 529-533, 1992.
Shimamoto et al. "Fertile Transgenic Rice Plants Regenerated From Transformed Protoplasts", Nature, 338: 274-276, Mar. 16, 1989.
Sigma-Aldrich "Innovations in Peptide Synthesis and Conjugation: Tools for Drug Discovery", ChemFiles, 5(12): 1-24, 2005.
Takahashi et al. "A New Method for the Formation of the ?-Glycose Bond of Sialyl Conjugates Based on Long-Range Participation", Tetrahedron Letters, XP004094811, 38(47): 8223-8226, Nov. 24, 1997. Fig.2, Compound 9.
Takahashi et al. "Design and Synthesis of a Water-Soluble Taxol Analogue: Taxol-Sialyl Conjugate", Bioorganic & Medicinal Chemistry Letters, XP004136633, 8(1-6): 113-116, Jan. 6, 1998. Fig.1, Compounds 1, 2.
Tardi et al. "Liposomal Encapsulation of Topotecan Enhances Anticancer Efficacy in Murine and Human Xenograft Models", Cancer Research, 60: 3389-3393, 2000.
Thermo Fisher Scientific "Instructions BM(PEG)2 and BM(PEG)3", Thermo Fisher Scientific Inc., Pierce Biotechnology, Rockford, IL, USA, 3 P., 2007.
Thermo Fisher Scientific "Instructions BS(PEG)n. Homofunctional, Amine-Reactive Crosslinkers With Polyethylene Glycol (PEG) Spacer Arms", Thermo Fisher Scientific Inc., Pierce Biotechnology, Rockford, IL, USA, 3 P., 2008.
UniProt "Name-ERABP1; OrderedLocusNames=At4g02980; ORFNames=T4I9.14; Arabidopsis Thaliana (Mouse-Ear Cress)", UniProtKB / Swiss-Prot, ID ABP1_ARATH, Accession No. P33487, Feb. 1, 1994.
Vamvakaki et al. "Fluorescence Detection of Enzymatic Activity Within a Liposome Based Nano-Biosensor", Biosensors and Bioelectronics 21: 384-388, 2005.
Vargas et al. "Endocytosis of Liposomes Containing Lyposomal Proteins Increases Intracellular Protein Degradation in growing L-132 Cells", European Journal of Biochemistry, 188: 99-109, 1990.
Yamaguchi et al. "Polysaccharide-Poly(Ethylene Glycol) Star Copolymer as a Scaffold for the Production of Bioactive Hydrogels", Biomacromolecules, 6: 1921-1930, 2005.
Zambrano et al. "Receptor Binding Activity and in Vitro Biological Activity of the Human FSH Charge Isoforms as Disclosed by Heterologous and Homologous Assay Systems. Implications for the Structure-Function Relationship of the FSH Variants", Endocrine, XP002554816, 10(2): 113-121, 1999. p. 114, col. 1, § 2, Fig.1.
International Preliminary Report on Patentability Dated Aug. 1, 2013 From the International Bureau of WIPO Re. Application No. PCT/IL2011/000719.
Official Action Dated Jul. 18, 2013 From the US Patent and Trademark Office Re. U.S. Appl. No. 13/582,464.
Wang et al. "Human Alpha-N-Acetylgalactosaminidase-Molecular Cloning, Nucleotide Sequence, and Expression of a Full-Length cDNA. Homology With Human Alpha-Galactosidase A Suggests Evolution From a Common Ancestral Gene", The Journal of Biological Chemistry, 265(35): 21859-21866, Dec. 15, 1990.
Communication Pursuant to Article 94(3) EPC Dated Jun. 18, 2015 From the European Patent Office Re. Application No. 11767776.5.
Notice of Reason for Rejection Dated Jun. 19, 2015 From the Japanese Patent Office Re. Application No. 2014-160449 and Its Translation Into English.
Notification of Office Action Dated Feb. 25, 2016 From the State Intellectual Property Office of the People's Republic of China Re. Application No. 201180069560.7 and Its Translation Into English.
Applicant-Initiated Interview Summary Dated May 22, 2015 From the US Patent and Trademark Office Re. U.S. Appl. No. 13/582,482.
Summons to Attend Oral Processings Pursuant to Rule 115(1) EPC Dated Mar. 31, 2016 From the European Patent Office Re. Application No. 11767776.5.
Notification of Office Action and Search Report Dated Jul. 31, 2015 From the State Intellectual Property Office of the People's Republic of China Re. Application No. 201180069560.7 and Its Translation Into English.
Yan et al. "Research Progress in the Linker of Fusion Protein", Biotchnology, 18(3): 92-94, Dec. 31, 2008. English Description.
European Search Report and the European Search Opinion Dated Sep. 13, 2016 From the European Patent Office Re. Application No. 16173953.7.
Official Action Dated Aug. 31, 2016 From the US Patent and Trademark Office Re. U.S. Appl. No. 14/936,720.
Translation of Decision on Rejection Dated Sep. 13, 2016 From the State Intellectual Property Office of the People's Republic of China Re. Application No. 201180069560.7.
Notice of Preliminary Rejection dated Apr. 18, 2017 From the Korean Patent Office Re. Application No. 2012-7025725 and Its Translation Into English. (9 Pages).

* cited by examiner

| | Name | Structure | Retention Time | GU | A-GAL batch A | A-GAL batch B |
|---|---|---|---|---|---|---|
| 1 | FcM2X | 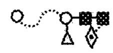 | 71.83 | 4.76 | NA | NA |
| 2 | M3X | 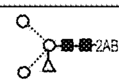 | 74.32 | 4.9 | 6.41 | 6.51 |
| 3 | M4 | 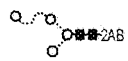 | 78.5 | 5.31 | 1.16 | 1.19 |
| 4 | FcM3 | 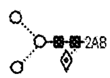 | 79.86 | 5.32 | 7.17 | 6.72 |
| 5 | FcM3X or M4X | 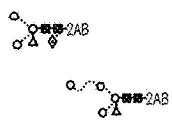 | 84.55 | 5.9 | 26.94 | 27.59 |
| 6 | M5 | 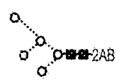 | 87.126 | 6.19 | 3.24 | 2.44 |
| 8 | M6 | 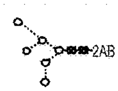 | 95.083 | 7.06 | 3.41 | 3.34 |
| 9 | M7 | 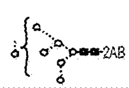 | 101.81 | 7.88 | 14.04 | 14.27 |
| 10 | M8 | 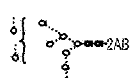 | 108.05 | 8.83 | 31.64 | 32.12 |
| 11 | M9 | 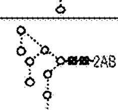 | 112.347 | 9.48 | 1.2 | 1.3 |

FIG. 8

NUCLEIC ACID CONSTRUCT FOR EXPRESSION OF ALPHA-GALACTOSIDASE IN PLANTS AND PLANT CELLS

RELATED APPLICATIONS

This application is a National Phase of PCT Patent Application No. PCT/IL2011/000719 having International filing date of Sep. 7, 2011, which is a Continuation-In-Part (CIP) of PCT Patent Application No. PCT/IL2011/000209 having International filing date of Mar. 2, 2011, and which claims the benefit of priority under 35 USC §119(e) of U.S. Provisional Patent Application Nos. 61/434,503 and 61/434,499, both filed on Jan. 20, 2011. The contents of the above applications are all incorporated by reference as if fully set forth herein in their entirety.

FIELD AND BACKGROUND OF THE INVENTION

The present invention, in some embodiments thereof, relates to a nucleic acid expression construct and, more particularly, but not exclusively, to a nucleic acid construct for expression of α-galactosidase in plant cells, cells expressing the nucleic acid construct and the human α-galactosidase, and uses thereof.

Fabry disease is an X-linked lysosomal storage disease that is caused by deficient activity of lysosomal enzyme α-galactosidase A (α-Gal A). Patients with classic Fabry disease typically have α-Gal A activity of less than 1% and often demonstrate the full spectrum of symptoms, including severe pain in the extremities (acroparesthesias), hypohidrosis, corneal and lenticular changes, skin lesions (angiokeratoma), renal failure, cardiovascular disease, pulmonary failure, neurological symptoms and stroke. In atypical Fabry disease, individuals with residual enzyme activity demonstrate symptoms later in life, and the symptoms are usually limited to one or a few organs. Clinical manifestations in female carriers vary greatly because of random X-chromosome inactivation. Although carriers commonly remain asymptomatic throughout life, many demonstrate clinical symptoms as variable and severe as those of affected males. De Duve first suggested that replacement of the missing lysosomal enzyme with exogenous biologically active enzyme might be a viable approach to treatment of lysosomal storage diseases [Fed Proc. 23:1045 (1964)].

Recombinant α-Galactosidase A for enzyme replacement therapy has been produced in insect (sf9) cells (see U.S. Pat. No. 7,011,831) in human fibroblasts (see U.S. Pat. No. 6,395,884) and in plant cells (see U.S. Pat. No. 6,846,968 and WO2008/132743). Clinical trials with recombinant α-Gal A (agalsidase beta [Fabrazyme®]: Genzyme Corporation, Cambridge, Mass.; agalsidase alfa [Replagal®]: Shire Human Genetic Therapies Corporation, Cambridge, Mass.) have been performed, and both drugs have been approved for clinical use. As of 2009, more than 2000 patients had been treated with either one of the two available formulations, and in general, safety and efficacy of both have been demonstrated (Hoffmann, Orphanet J Rare Dis. 2009; 4:21).

Clinical experience has indicated that the available recombinant enzyme compositions differ with regard to patient tolerance, immunogenicity, dosage regimen and clinical efficacy (Hoffmann, Orphanet J Rare Dis. 2009; 4:21). Another drawback associated with the existing recombinant enzymes is their expense, which can place a heavy economic burden on health care systems. The high cost of these recombinant enzymes, when produced in mammalian cell cultures, bioreactors or insect cells results from a complex purification and modification protocol, and the relatively large amounts of the therapeutic required for existing treatments. There is therefore, an urgent need to reduce the cost of α-galactosidase so that this life saving therapy can be provided more affordably to all who require it.

Human lysosomal enzymes can be produced in transgenic plants in order to solve problems of safety, viral infections, immune reactions, production yield and cost. US 2002/0088024 teaches expression in plant cells of recombinant human α-galactosidase, using a rice-amylase ER targeting signal peptide, and a human α-galactosidase coding sequence truncated at the C-terminal portion for efficient expression and secretion into the intracellular fluid.

WO 97/10353 teaches production of lysosomal enzymes in plants, specifically IDUA and glucocerebrosidase, using the wound-induced MeGA promoter and FLAG tag for recovery. WO 97/10353 does not provide guidance for specific constructs expressing recombinant human α-galactosidase.

Cramer et al. (Curr. Topics Trans. 1999 Plants 95-118) reviews methods of expression of glucocerebrosidase and IDUA in plants in a similar manner as WO 97/10353, that is in the endomembrane (IF) of tobacco leaves, and describes plant expression in general but does not provide guidance for expression of human recombinant α-galactosidase.

US2006-0204487 teaches methods for the expression of human lysosomal enzymes in plants, employing a variety of strategies for targeting the recombinant polypeptides (specifically, glucocerebrosidase) for efficient glycosylation and glycan remodeling. Cloning and expression of recombinant human α-galactosidase from specific constructs is not disclosed.

WO2007/010533 teaches the administration of plant cells expressing recombinant bioactive molecules, for example, lysosomal enzymes such as human glucocerebrosidase and human α-galactosidase. Cloning and expression of recombinant human α-galactosidase is not disclosed.

WO2008/132743 describes cloning of a human α-galactosidase coding sequence into a plant expression vector, and its expression in tobacco cells, resulting in a biologically active, full length glycosylated α-galactosidase enzyme which demonstrated uptake in fibroblasts. However, more advanced α-galactosidase expression vectors for yet further increased efficiency of expression and production of recombinant human α-galactosidase protein having improved pharmacokinetics under clinical conditions are needed.

SUMMARY OF THE INVENTION

According to an aspect of some embodiments of the present invention there is provided a nucleic acid expression construct, the construct comprising a nucleic acid sequence encoding a human α-galactosidase protein, wherein the human α-galactosidase protein is translationally fused at the N-terminal to an *Arabidopsis* ABPI endoplasmic reticulum targeting signal peptide and wherein the human α-galactosidase protein is translationally fused at the C-terminal to an endoplasmic reticulum retention signal peptide.

According to an aspect of some embodiments of the present invention there is provided a human α-galactosidase protein having an N-terminal Glycine residue, wherein the human α-galactosidase protein is translationally fused at the C-terminal to an endoplasmic reticulum retention signal peptide.

According to some embodiments of the invention, the nucleic acid sequence comprises SEQ ID NO: 22.

According to some embodiments of the invention, the *Arabidopsis* ABPI endoplasmic reticulum targeting signal peptide is as set forth in SEQ ID NO: 4.

According to some embodiments of the invention, the nucleic acid construct comprises a nucleic acid sequence encoding the endoplasmic reticulum targeting signal peptide as set forth in SEQ ID NO: 5.

According to some embodiments of the invention, the endoplasmic reticulum retention signal peptide is as set forth in SEQ ID NO: 6.

According to some embodiments of the invention, the nucleic acid construct comprises a nucleic acid sequence encoding the endoplasmic reticulum retention peptide as set forth in SEQ ID NO: 19.

According to some embodiments of the invention, the nucleic acid sequence has a sequence as set forth in SEQ ID NO: 2

According to some embodiments of the invention, the human α-galactosidase protein has an amino acid sequence as set forth in SEQ ID NO: 1.

According to some embodiments of the invention, a codon usage of the nucleic acid sequence is optimized for *Nicotinia tabaccum*.

According to some aspects of some embodiments of the invention there is provided an isolated cell comprising the nucleic acid construct of the invention.

According to some embodiments of the invention, the cell recombinantly produces the human α-galactosidase enzyme.

According to some embodiments of the invention, the human α-galactosidase comprises an N-terminal Glycine residue.

According to some embodiments of the invention, the cell is a plant cell.

According to some embodiments of the invention, the plant cell is a tobacco cell.

According to some embodiments of the invention, the tobacco cell is a BY-2 cell.

According to some embodiments of the invention, the human α-galactosidase protein is recombinantly produced so as to have at least one exposed mannose residue.

According to some embodiments of the invention, the human α-galactosidase protein is recombinantly produced so as to have at least one core β-(1,2) xylose or at least one core α-(1,3) fucose or both.

According to some embodiments of the invention, the nucleic acid construct is stably integrated into the genome of the cell.

According to some embodiments of the invention, the cell is an *Agrobacterium tumefaciens* cell.

According to an aspect of some embodiments of the present invention there is provided a method of producing a recombinant human α-galactosidase protein, comprising: providing a cell according to the invention; and growing the cell so as to produce the recombinant human α-galactosidase protein; and isolating the recombinant human α-galactosidase protein from the cell.

According to some embodiments of the invention, the cell is an isolated cell cultured in a cell culture medium.

According to some embodiments of the invention, the culturing is affected in a disposable bioreactor.

According to some embodiments of the invention, the human α-galactosidase protein, has an amino acid sequence as set forth in SEQ ID NO: 16.

According to an aspect of some embodiments of the present invention there is provided a pharmaceutical composition comprising, as an active ingredient, the human α-galactosidase protein of the present invention and a pharmaceutically acceptable carrier.

According to an aspect of some embodiments of the present invention there is provided a pharmaceutical composition comprising, as an active ingredient, the cell of the present invention and a pharmaceutically acceptable carrier.

According to an aspect of some embodiments of the present invention there is provided a pharmaceutical composition comprising, as an active ingredient, a population of human α-galactosidase proteins of the invention, wherein the predominant glycan structures of said population of human α-galactosidase proteins are mannose 4-β-(1,2) xylose (M4X); mannose 3-β(1,2) xylose-α-(1,3) fucose [Fc(3)M3X] and mannose 8 (M8), and a pharmaceutically acceptable carrier.

According to an aspect of some embodiments of the present invention there is provided a method of treating Fabry's disease in subject in need thereof, comprising administering to the subject the pharmaceutical composition of the invention.

According to an aspect of some embodiments of the present invention there is provided a pharmaceutical composition comprising the human α-galactosidase protein of the invention, having a glycan structure comprising nine mannose residues, wherein three are exposed mannose residues, and a pharmaceutically acceptable carrier. The human α-galactosidase protein having a glycan structure comprising nine mannose residues, wherein three are exposed mannose residues can be 0.5%, 0.8%, 1.0%, 1.3%, 2% or more of the population of human α-galactosidase proteins of the composition.

According to an aspect of some embodiments of the present invention there is provided a method of treating Fabry's disease in subject in need thereof, comprising administering to the subject the pharmaceutical composition comprising the cell of the invention.

According to an aspect of some embodiments of the present invention there is provided the use of the human α-galactosidase protein of the invention for the manufacture of a medicament for the treatment of Fabry's disease in a subject in need thereof.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1:

FIG. 1 is an amino acid sequence alignment of the α-galactosidase encoded by the nucleic acid of the invention (SEQ ID NO: 1, lower sequence), and native human α-galactosidase protein (GenBank: X05790, upper sequence), including the native signal leader peptide (SEQ ID NO: 3, highlighted in red). The *Arabidopsis* ABPI endoplasmic reticulum targeting signal peptide (SEQ ID NO: 4) is highlighted in green. The SEKDEL endoplasmic reticulum retention signal peptide (SEQ ID NO: 6) is located at the C-terminus of the plant-expressed protein. The mature native α-galactosidase enzyme protein sequence (SEQ ID NO: 7) is highlighted in yellow.

Figure 2:
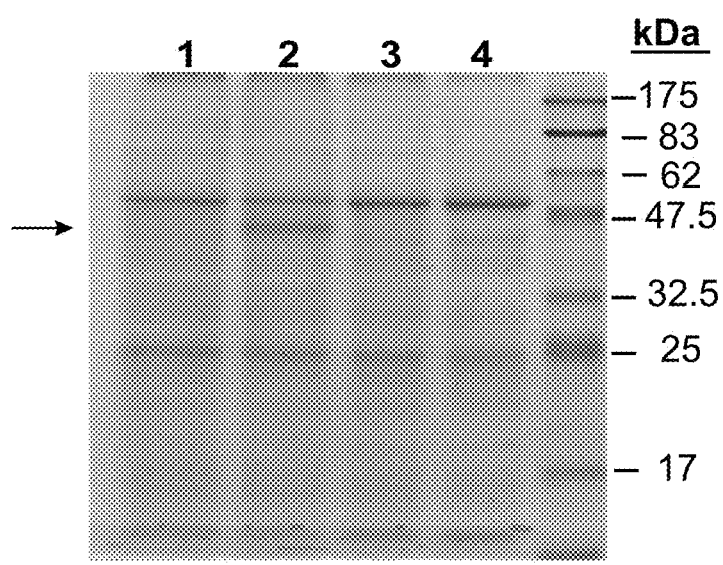
Figure 3:
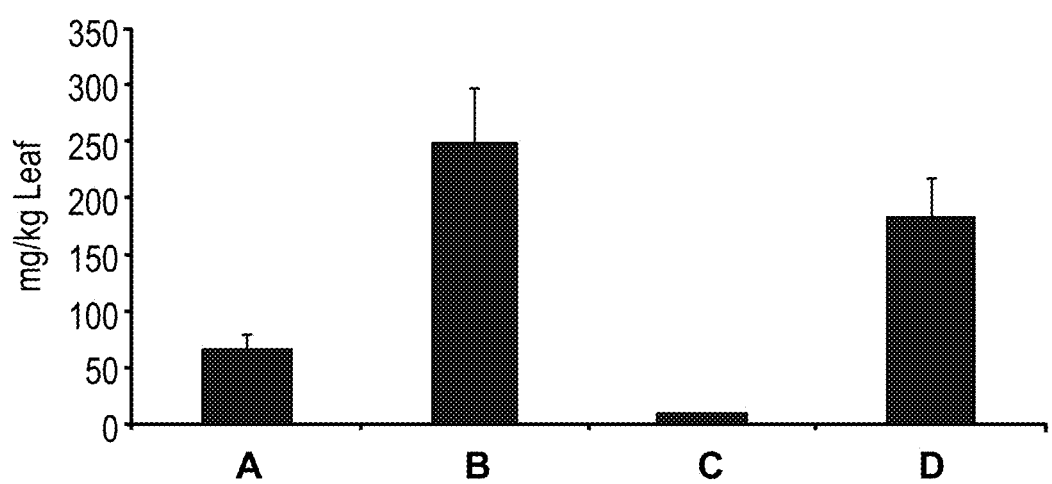
Figure 4:
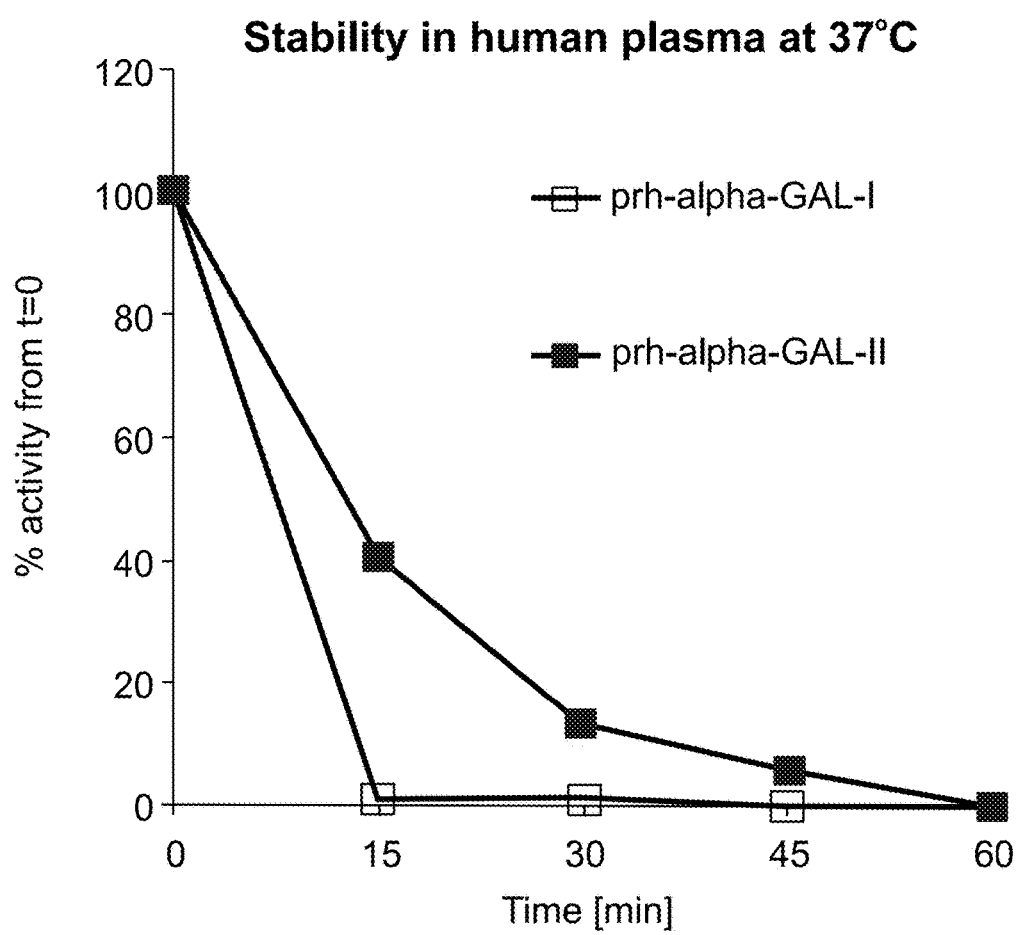
Figure 5:
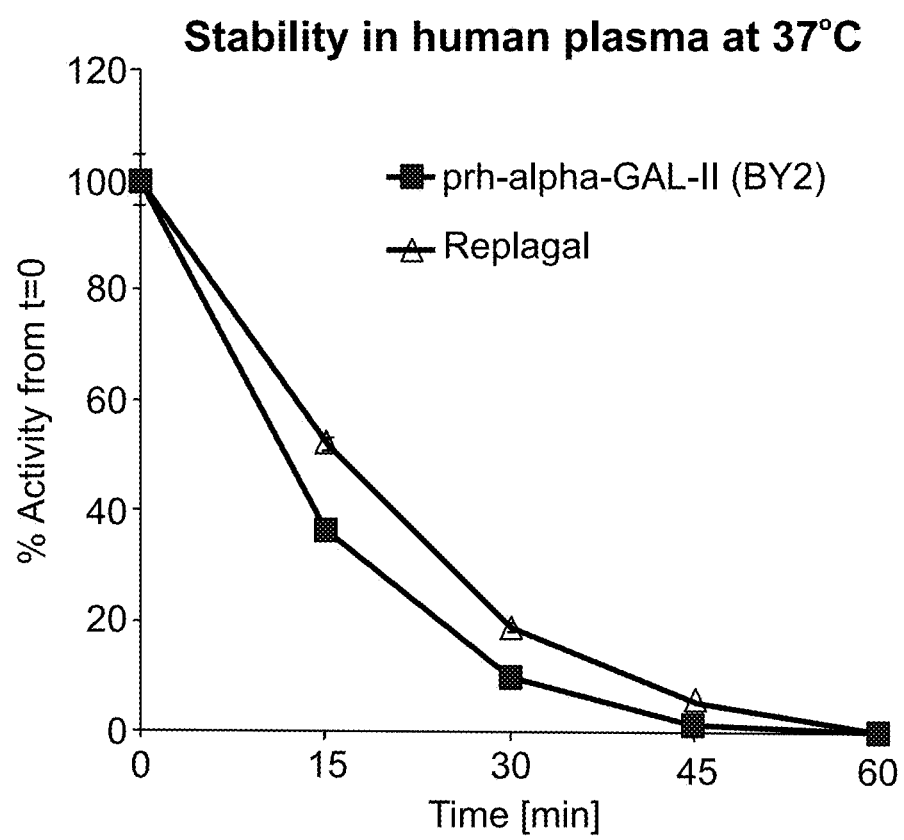
Figure 6:
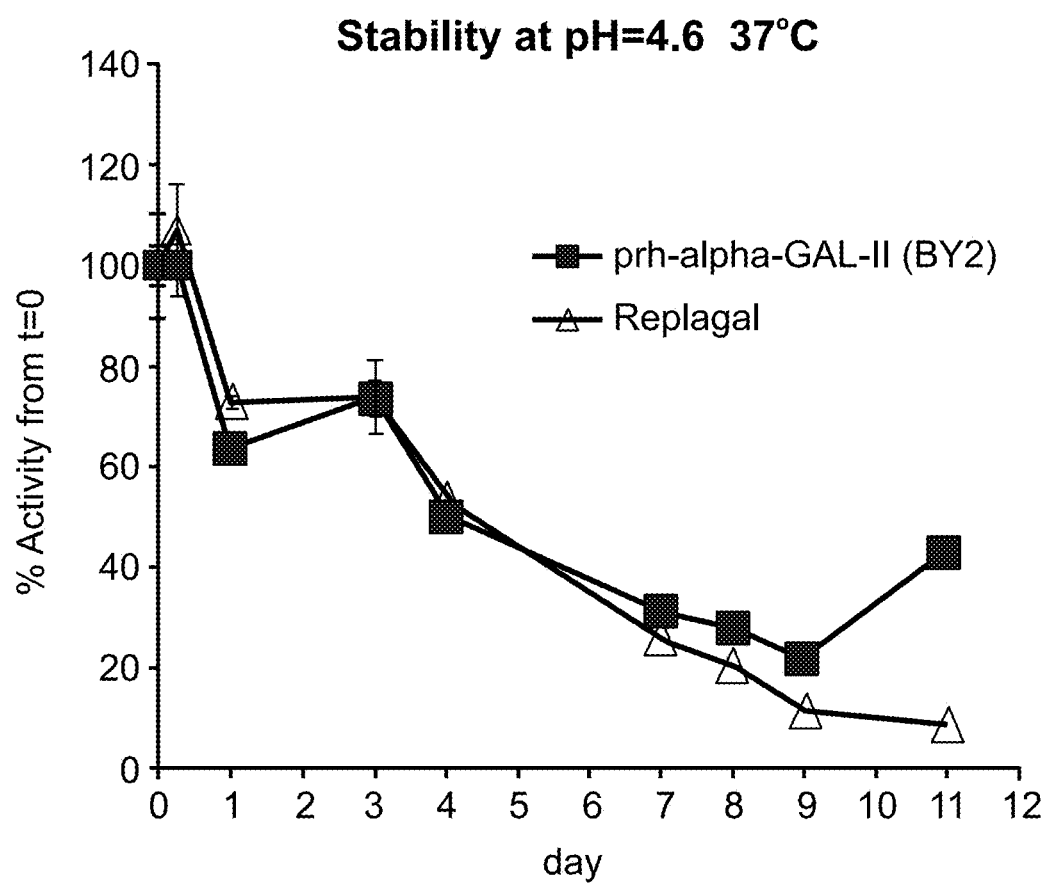
Figure 7:
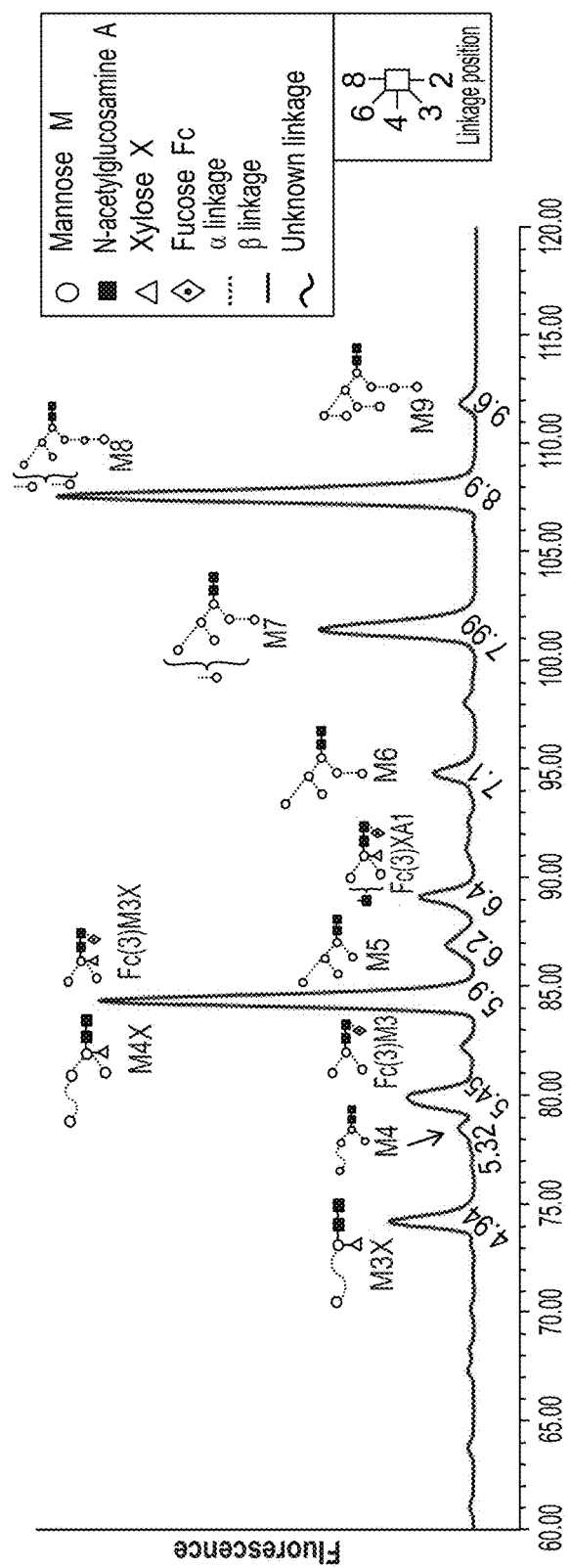

FIG. 2 is a scan of an SDS-PAGE gel illustrating expression levels of diverse human α-galactosidase constructs in plants. Extracts of leaves from *N. benthamaina* plants infiltrated with different human α-galactosidase constructs were separated on a 12% SDS-PAGE reduced gel, and stained with Coomassie Blue for visualization of protein. Lane 1=products of expression of a construct (SEQ ID NO:8) encoding an α-galactosidase with an apple pectinase endoplasmic reticulum targeting signal peptide (apple pectinase signal peptide=SEQ ID NO: 9). Lane 2=products of expression of SEQ ID NO: 2, encoding an α-galactosidase with an ABPI endoplasmic reticulum targeting signal peptide (ABPI signal peptide=SEQ ID NO: 4). Lane 3=products of expression of SEQ ID NO: 11, encoding SEQ ID NO:12 with an apple pectinase endoplasmic reticulum targeting signal peptide (SEQ ID NO: 9). Lane 4=Negative (no α-galactosidase coding sequence) control. Prominent band in lane 2 (arrow) corresponds to size of the mature recombinant α-galactosidase monomer (SEQ ID NO: 21). Coomassie stained band indicates abundant α-galactosidase protein;

FIG. 3 is a histogram demonstrating levels of catalytic activity in extracts of plants expressing diverse human α-galactosidase constructs. Leaves from *N. benthamaina* plants were infiltrated with different human α-galactosidase constructs as follows: A=SEQ ID NO: 8, encoding an α-galactosidase protein with an apple pectinase endoplasmic reticulum targeting signal peptide (apple pectinase signal peptide=SEQ ID NO: 9). B=SEQ ID NO: 2, encoding an α-galactosidase protein with an ABPI endoplasmic reticulum targeting signal peptide (ABPI signal peptide=SEQ ID NO: 4). C=SEQ ID NO: 13, encoding an α-galactosidase protein with an endochitinase B endoplasmic reticulum targeting signal peptide (endochitinase signal protein=SEQ ID NO: 14). D=SEQ ID NO: 11, encoding an α-galactosidase protein (SEQ ID NO: 12) with an apple pectinase endoplasmic reticulum targeting signal peptide (apple pectinase signal sequence=SEQ ID NO: 9). Leaves from the respective plants were extracted in activity assay buffer, and catalytic activity determined using p-nitrophenylalpha-D-galactopyranoside (pNP-alpha-D-Gal, GBB1290, IRIS Biotech, Germany) as a hydrolysis substrate. Generation of the p-nitrophenolate chromophore was monitored at 405 nm;

FIG. 4 is a graph comparing stability of two plant recombinant human α-galactosidases in human plasma (37° C.) measured by residual catalytic activity. α-galactosidase from leaves of *N. benthamaina* plants transformed with SEQ ID NO: 11, encoding SEQ ID NO:12 with an apple pectinase endoplasmic reticulum targeting signal peptide (open squares) and α-galactosidase from leaves of *N. benthamaina* plants transformed with SEQ ID NO: 2, encoding an α-galactosidase (SEQ ID NO: 1) having an ABPI endoplasmic reticulum targeting signal peptide (closed squares) was purified by plant disruption, salting out and chromatography, and incubated in human plasma at 37° C. for up to 1 hour, to simulate in-vivo pharmacokinetics. Samples were assayed for α-galactosidase catalytic activity by the PNP-G assay at indicated intervals. Note the greater stability of α-galactosidase from leaves of *N. benthamaina* plants expressing SEQ ID NO: 1 (closed squares);

FIG. 5 is a graph comparing stability of catalytic activity of the plant cell expressed α-galactosidase (closed squares) with that of commercial human recombinant α-galactosidase expressed in human cell culture (Replagal®, open triangles). Unpurified extract of BY2 cells expressing SEQ ID NO: 2, encoding an α-galactosidase (SEQ ID NO: 1) having an ABPI endoplasmic reticulum targeting signal peptide (closed squares) and human recombinant α-galactosidase expressed in mammalian cell culture (Replagal®, open triangles), were incubated in plasma at 37° C. for up to 1 hour, to simulate in-vivo pharmacokinetics. Samples were assayed for α-galactosidase catalytic activity by the PNP-G assay at indicated intervals. Note the similar stability of the plant-cell-expressed and human-cell-expressed enzymes;

FIG. 6 is a graph comparing stability of catalytic activity of the plant expressed α-galactosidase (closed squares) with that of commercial human recombinant α-galactosidase expressed in human cell culture (Replagal®, open triangles). Unpurified extract of BY2 cells expressing SEQ ID NO: 2, encoding an α-galactosidase (SEQ ID NO: 1) having an ABPI endoplasmic reticulum targeting signal peptide (closed squares) and human recombinant α-galactosidase expressed in mammalian cell culture (Replagal®, open triangles), were incubated under conditions simulating the lysosomal environment [acidic (pH 4.6)] at 37° C. for up to 11 days. Samples were assayed for α-galactosidase catalytic activity by the PNP-G assay at indicated intervals, when incubated. Note the similar stability of the plant-expressed and mammalian-expressed enzymes for up to 9 days;

FIG. 7 is chromogram showing the distribution of glycan structures in the products of glycosylase digests of plant cell expressed α-galactosidase. Samples of extract of BY2 cells expressing SEQ ID NO: 2, encoding an α-galactosidase (SEQ ID NO: 1) having an ABPI endoplasmic reticulum targeting signal peptide were reduced, alkylated and separated on SDS-PAGE. The protein bands were taken for glycan analysis by trypsin digestion followed by both PNGase A and PNGase F digestion. The resulting free glycans were extracted, purified, labeled with the fluorescent reagent anthranilamide (2AB), separated using a TSK gel Amide 80 normal phase HPLC, and detected using a fluorescence detector. Note major peaks at 5.9 and 8.9 GU (84.55 minutes and 108.05 minutes), and a minor peak of M9 at 112.35;

FIG. 8 is a table showing the glycan profile the plant cell expressed α-galactosidase, expressed as the percent area of the individual glycans represented in the chromogram of FIG. 7. Note the identical profiles of each independent analysis (A and B).

DESCRIPTION OF SPECIFIC EMBODIMENTS OF THE INVENTION

The present invention, in some embodiments thereof, relates to an expression vector for recombinant expression of human α-galactosidase in plant cells, methods for its expression thereof in plant cells and the human α-galactosidase produced thereby.

It is to be understood that the invention is not necessarily limited in its application to the details set forth in the following description or exemplified by the Examples. The invention is capable of other embodiments or of being practiced or carried out in various ways.

The present inventors have constructed an expression vector for recombinant expression of human α-galactosidase in plant cells, transformed tobacco plants and plant cells with the vector, and have isolated catalytically active human α-galactosidase from the plants and cell cultures. The expressed recombinant human α-galactosidase retained favorable catalytic activity under conditions simulating those normally encountered in in-vivo administration, suggesting improved simulated pharmacokinetics as compared to other plant derived recombinant human α-galactosidase, and similar to those of mammalian-expressed recombinant human α-galactosidase (Replagal®).

Thus, according to one aspect of the present invention, there is provided a nucleic acid expression construct, the construct comprising a nucleic acid sequence encoding a human α-galactosidase protein, wherein the human α-galactosidase protein is translationally fused at the N-terminal to an *Arabidopsis* ABPI endoplasmic reticulum targeting signal peptide and wherein the human α-galactosidase protein is translationally fused at the C-terminal to an endoplasmic reticulum retention signal peptide.

As used herein the term "human α-galactosidase protein" refers to a human α-galactosidase A (α-D-galactoside galactohydrolase; EC 3.2.1.22; α-Gal A) polypeptide. According to some embodiments of the invention, the human α-galactosidase protein is the mature human α-galactosidase protein, having the amino acid sequence as set forth in SEQ ID NO: 7 (mature human A-Gal). It will be appreciated that the human α-galactosidase protein can be a modified human α-galactosidase protein, having an amino acid sequence different than that of SEQ ID NO: 7. One non-limiting example of a modified human α-galactosidase protein encoded by the expression vector of the invention is SEQ ID NO: 16 (G-A-Gal). In another non-limiting example the human α-galactosidase protein encoded by the expression vector can be a mixture of human α-galactosidase proteins comprising both α-galactosidase proteins having an N-terminal glycine residue (G), such as SEQ ID NO: 16 or SEQ ID NO: 21, and absent an N-terminal glycine residue, such as, but not limited to SEQ ID NO: 7 and SEQ ID NO: 20.

According to another aspect of the invention, the human α-galactosidase protein is translationally fused at the N-terminal to an *Arabidopsis* ABPI endoplasmic reticulum targeting signal peptide and the human α-galactosidase protein is also translationally fused at the C-terminal to an endoplasmic reticulum retention signal peptide.

As used herein the term "translationally fused at the N-terminal" or "translationally fused at the C-terminal" refers to covalent attachment of the indicated peptide via a peptide bond to the N-terminal or C-terminal amino acid of the mature human α-galactosidase protein typically as a result of recombinant expression.

As used herein, the term "*Arabidopsis* ABPI endoplasmic reticulum targeting signal peptide" refers to the leader peptide sequence of the *Arabidopsis thaliana* auxin binding protein (Uni-Prot Accession No. P33487), which is capable of directing the expressed protein to the endoplasmic reticulum within the plant cell. In one embodiment, the *Arabidopsis* ABPI endoplasmic reticulum targeting signal peptide is a 33 amino acid polypeptide as set forth in SEQ ID NO: 4.

As used herein, the term "endoplasmic reticulum retention signal peptide" refers to a peptide sequence which, when present at the N- or C-terminus of a polypeptide, causes the polypeptide to be retrieved from the Golgi apparatus, and retained in the endoplasmic reticulum (see Rayon et al. Journal of Experimental Botany, Vol. 49, No. 326, pp. 1463-1472, 1998; and Neumann, et al Annals of Botany, 2003; 92:167-180). In one embodiment, the endoplasmic reticulum retention signal peptide is KDEL (SEQ ID NO: 17) or SEKDEL (SEQ ID NO: 6). Other suitable plant endoplasmic reticulum signals are known in the art (see Pagny et al, Journal of Experimental Botany, Vol. 50, pp. 157-64).

Thus, according to an embodiment of the present invention, the human α-galactosidase protein translationally fused at the N-terminal to an *Arabidopsis* ABPI endoplasmic reticulum targeting signal peptide and the human α-galactosidase protein and translationally fused at the C-terminal to an endoplasmic reticulum retention signal peptide has an amino acid sequence as set forth in SEQ ID NO: 1.

As used herein the term "nucleic acid sequence" refers to a single or double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the above).

As used herein the phrase "complementary polynucleotide sequence" refers to a sequence, which results from reverse transcription of messenger RNA using a reverse transcriptase or any other RNA dependent DNA polymerase. Such a sequence can be subsequently amplified in vivo or in vitro using a DNA dependent DNA polymerase.

As used herein the phrase "genomic polynucleotide sequence" refers to a sequence derived (isolated) from a chromosome and thus it represents a contiguous portion of a chromosome.

As used herein the phrase "composite polynucleotide sequence" refers to a sequence, which is at least partially complementary and at least partially genomic. A composite sequence can include some exonal sequences required to encode the polypeptide of the present invention, as well as some intronic sequences interposing therebetween. The intronic sequences can be of any source, including of other genes, and typically will include conserved splicing signal sequences. Such intronic sequences may further include cis acting expression regulatory elements.

According to some embodiments of the present invention, the nucleic acid sequences encoding the polypeptides of the present invention are optimized for expression. Examples of such sequence modifications include, but are not limited to, an altered G/C content to more closely approach that typically found in the plant species of interest, and the removal of codons atypically found in the plant species commonly referred to as codon optimization. In one embodiment, the codon usage of the nucleic acid sequence encoding the human α-galactosidase protein translationally fused at the N-terminal to an *Arabidopsis* ABPI endoplasmic reticulum targeting signal peptide and the human α-galactosidase protein and translationally fused at the C-terminal to an endoplasmic reticulum retention signal peptide is optimized for *Nicotiana tobacuum* or *Nicotiana benthamiana*.

The phrase "codon optimization" refers to the selection of appropriate DNA nucleotides for use within a structural gene or fragment thereof that approaches codon usage within the plant of interest. Therefore, an optimized gene or nucleic acid sequence refers to a gene in which the nucleotide sequence of a native or naturally occurring gene has been modified in order to utilize statistically-preferred or statistically-favored codons within the plant. The nucleotide sequence typically is examined at the DNA level and the coding region optimized for expression in the plant species determined using any suitable procedure, for example as described in Sardana et al. (1996, Plant Cell Reports 15:677-681). In this method, the standard deviation of codon usage, a measure of codon usage bias, may be calculated by first finding the squared proportional deviation of usage of each codon of the native gene relative to that of highly expressed plant genes, followed by a calculation of the average squared deviation. The formula used is: 1 SDCU=n=1 N[(Xn−Yn)/Yn]2/N, where Xn refers to the frequency of usage of codon n in highly expressed plant genes, where Yn to the frequency of usage of codon n in the gene of interest and N refers to the total number of codons in the gene of interest. A Table of codon usage from highly expressed genes of dicotyledonous plants is compiled using the data of Murray et al. (1989, Nuc Acids Res. 17:477-498).

One method of optimizing the nucleic acid sequence in accordance with the preferred codon usage for a particular plant cell type is based on the direct use, without performing any extra statistical calculations, of codon optimization Tables such as those provided on-line at the Codon Usage Database through the NIAS (National Institute of Agrobiological Sciences) DNA bank in Japan (Hypertext Transfer protocol://World Wide Web (dot) kazusa (dot) or (dot) jp/codon/). The Codon Usage Database contains codon usage tables for a number of different species, with each codon usage Table having been statistically determined based on the data present in Genbank.

By using the above Tables to determine the most preferred or most favored codons for each amino acid in a particular species (for example, rice), a naturally-occurring nucleotide sequence encoding a protein of interest can be codon optimized for that particular plant species. This is effected by replacing codons that may have a low statistical incidence in the particular species genome with corresponding codons, in regard to an amino acid, that are statistically more favored. However, one or more less-favored codons may be selected to delete existing restriction sites, to create new ones at potentially useful junctions (5' and 3' ends to add signal peptide or termination cassettes, internal sites that might be used to cut and splice segments together to produce a correct full-length sequence), or to eliminate nucleotide sequences that may negatively effect mRNA stability or expression.

The desired encoding nucleotide sequence may already, in advance of any modification, contain a number of codons that correspond to a statistically-favored codon in a particular plant species. Therefore, codon optimization of the native nucleotide sequence may comprise determining which codons, within the desired nucleotide sequence, are not statistically-favored with regards to a particular plant, and modifying these codons in accordance with a codon usage table of the particular plant to produce a codon optimized derivative. A modified nucleotide sequence may be fully or partially optimized for plant codon usage provided that the protein encoded by the modified nucleotide sequence is produced at a level higher than the protein encoded by the corresponding naturally occurring or native gene. Construction of synthetic genes by altering the codon usage is described in for example PCT Patent Application 93/07278.

According to some embodiments of the invention, the human α-galactosidase protein is encoded by a nucleic acid sequence as set forth in SEQ ID NO: 18. According to further embodiments of the invention, the *Arabidopsis* ABPI endoplasmic reticulum targeting signal peptide is encoded by a nucleic acid sequence as set forth in SEQ ID NO: 5. According to yet further embodiments of the invention the endoplasmic reticulum retention signal peptide is encoded by a nucleic acid sequence as set forth in SEQ ID NO: 19. According to still further embodiments of the invention the human α-galactosidase protein translationally fused at the N-terminal to an *Arabidopsis* ABPI endoplasmic reticulum targeting signal peptide and the human α-galactosidase protein and translationally fused at the C-terminal to an endoplasmic reticulum retention signal peptide is encoded by a nucleic acid sequence as set forth in SEQ ID NO: 2.

As used herein the term "nucleic acid expression construct" refers to a nucleic acid construct which includes the nucleic acid of some embodiments of the invention (e.g., SEQ ID NO: 2) and at least one promoter for directing transcription of nucleic acid in a host plant cell. Further details of suitable transformation approaches are provided hereinbelow.

According to some embodiments of the invention, there is provided a nucleic acid expression construct comprising the nucleic acid sequence of the invention, and a promoter for directing transcription of the nucleic acid sequence in a plant host cell.

According to some embodiments of the invention, the nucleic acid is operably linked to the promoter sequence.

A coding nucleic acid sequence is "operably linked" to a regulatory sequence (e.g., promoter) if the regulatory sequence is capable of exerting a regulatory effect on the coding sequence linked thereto.

Any suitable promoter sequence can be used by the nucleic acid construct of the present invention. Preferably the promoter is a constitutive promoter, a tissue-specific, or an inducible promoter.

As used herein the phrase "plant-expressible" refers to a promoter sequence, including any additional regulatory elements added thereto or contained therein, is at least capable of inducing, conferring, activating or enhancing expression in a plant cell, tissue or organ, preferably a monocotyledonous or dicotyledonous plant cell, tissue, or organ. Such a promoter can be constitutive, i.e., capable of directing high level of gene expression in a plurality of tissues, tissue specific, i.e., capable of directing gene expression in a particular tissue or tissues, inducible, i.e., capable of directing gene expression under a stimulus, or chimeric, i.e., formed of portions of at least two different promoters.

Examples of preferred promoters useful for the methods of some embodiments of the invention are presented in Table I, II, III and IV.

TABLE I

Exemplary constitutive promoters for use in the performance of some embodiments of the invention

| Gene Source | Expression Pattern | Reference |
|---|---|---|
| Actin | constitutive | McElroy etal, Plant Cell, 2: 163-171, 1990 |
| CAMV 35S | constitutive | Odell et al, Nature, 313: 810-812, 1985 |
| CaMV 19S | constitutive | Nilsson et al., Physiol. Plant 100: 456-462, 1997 |
| GOS2 | constitutive | de Pater et al, Plant J Nov; 2(6): 837-44, 1992 |
| ubiquitin | constitutive | Christensen et al, Plant Mol. Biol. 18: 675-689, 1992 |
| Rice cyclophilin | constitutive | Bucholz et al, Plant Mol Biol. 25(5): 837-43, 1994 |
| Maize H3 histone | constitutive | Lepetit et al, Mol. Gen. Genet. 231: 276-285, 1992 |
| Actin 2 | constitutive | An et al, Plant J. 10(1); 107-121, 1996 |

TABLE II

Exemplary seed-preferred promoters for use in the performance of some embodiments of the invention

| Gene Source | Expression Pattern | Reference |
|---|---|---|
| Seed specific genes | seed | Simon, et al., Plant Mol. Biol. 5. 191, 1985; Scofield, etal., J. Biol. Chem. 262: 12202, 1987.; Baszczynski, et al., Plant Mol. Biol. 14: 633, 1990. |
| Brazil Nut albumin | seed | Pearson' et al., Plant Mol. Biol. 18: 235-245, 1992. |
| legumin | seed | Ellis, et al. Plant Mol. Biol. 10: 203-214, 1988 |
| Glutelin (rice) | seed | Takaiwa, et al., Mol. Gen. Genet. 208: 15-22, 1986; Takaiwa, et al., FEBS Letts. 221: 43-47, 1987 |
| Zein | seed | Matzke et al Plant Mol Biol, 143). 323-32 1990 |
| napA | seed | Stalberg, et al, Planta 199: 515-519, 1996 |
| wheat LMW and HMW, glutenin-1 | endosperm | Mol Gen Genet 216: 81-90, 1989; NAR 17: 461-2, |
| Wheat SPA | seed | Albanietal, Plant Cell, 9: 171-184, 1997 |
| wheat a, b and g gliadins | endosperm | EMBO3: 1409-15, 1984 |
| Barley ltr1 promoter | endosperm | |
| barley B1, C, D hordein | endosperm | Theor Appl Gen 98: 1253-62, 1999; Plant J 4: 343-55, 1993; Mol Gen Genet 250: 750-60, 1996 |
| Barley DOF | endosperm | Mena et al, The Plant Journal, 116(1): 53-62, 1998 |
| Biz2 | endosperm | EP99106056.7 |
| Synthetic promoter | endosperm | Vicente-Carbajosa et al., Plant J. 13: 629-640, 1998 |
| rice prolamin NRP33 | endosperm | Wu et al, Plant Cell Physiology 39(8) 885-889, 1998 |
| rice -globulin Glb-1 | endosperm | Wu et al, Plant Cell Physiology 398) 885-889, 1998 |
| rice OSH1 | embryo | Sato et al, Proc. Nati. Acad. Sci. USA, 93: 8117-8122 |
| rice alpha-globulin REB/OHP-1 | endosperm | Nakase et al. Plant Mol. Biol. 33: 513-S22, 1997 |
| rice ADP-glucose PP | endosperm | Trans Res 6: 157-68, 1997 |
| maize ESR gene family | endosperm | Plant J 12: 235-46, 1997 |
| sorghum gamma-kafirin | endosperm | PMB 32: 1029-35, 1996 |
| KNOX | emryo | Postma-Haarsma ef al, Plant Mol. Biol. 39: 257-71, 1999 |
| rice oleosin | Embryo and aleuton | Wu et at, J. Biochem., 123: 386, 1998 |
| sunflower oleosin | Seed (embryo and dry seed) | Cummins, etal., Plant Mol. Biol. 19: 873-876, 1992 |

TABLE III

Exemplary flower-specific promoters for use in the performance of the invention

| Gene Source | Expression Pattern | Reference |
|---|---|---|
| AtPRP4 | flowers | www.salus. medium.edu/mmg/tierney/html |
| chalene synthase (chsA) | flowers | Van der Meer, et al., Plant Mol. Biol. 15, 95-109, 1990. |
| LAT52 | anther | Twell et al Mol. Gen Genet. 217: 240-245 (1989) |
| apetala- 3 | flowers | |

TABLE IV

Alternative rice promoters for use in the performance of the invention

| PRO # | gene | expression |
|---|---|---|
| PR00001 | Metallothionein Mte | transfer layer of embryo + calli |
| PR00005 | putative beta-amylase | transfer layer of embryo |
| PR00009 | Putative cellulose synthase | Weak in roots |
| PR00012 | lipase (putative) | |
| PR00014 | Transferase (putative) | |
| PR00016 | peptidyl prolyl cis-trans isomerase (putative) | |
| PR00019 | unknown | |
| PR00020 | prp protein (putative) | |
| PR00029 | nodulinc (putative) | |
| PR00058 | Proteinase inhibitor Rgpi9 | seed |
| PR00061 | beta expansine EXPB9 | Weak in young flowers |
| PR00063 | Structural protein | young tissues + calli + embryo |
| PR00069 | xylosidase (putative) | |
| PR00075 | Prolamine 10Kda | strong in endosperm |
| PR00076 | allergen RA2 | strong in endosperm |
| PR00077 | prolamine RP7 | strong in endosperm |
| PR00078 | CBP80 | |
| PR00079 | starch branching enzyme I | |
| PR00080 | Metallothioneine-like ML2 | transfer layer of embryo + calli |
| PR00081 | putative caffeoyl- CoA 3-0 methyltransferase | shoot |
| PR00087 | prolamine RM9 | strong in endosperm |
| PR00090 | prolamine RP6 | strong in endosperm |
| PR00091 | prolamine RP5 | strong in endosperm |
| PR00092 | allergen RA5 | |
| PR00095 | putative methionine aminopeptidase | embryo |
| PR00098 | ras-related GTP binding protein | |
| PR00104 | beta expansine EXPB1 | |
| PR00105 | Glycine rich protein | |
| PR00108 | metallothionein like protein (putative) | |
| PR00110 | RCc3 strong root | |
| PR00111 | uclacyanin 3-like protein | weak discrimination center/shoot meristem |
| PR00116 | 26S proteasome regulatory particle non-ATPase subunit 11 | very weak meristem specific |
| PR00117 | putative 40S ribosomal protein | weak in endosperm |
| PR00122 | chlorophyll a/lo-binding protein precursor (Cab27) | very weak in shoot |
| PR00123 | putative protochlorophyllide reductase | Strong leaves |
| PR00126 | metallothionein RiCMT | strong discrimination center shoot meristem |
| PR00129 | GOS2 | Strong constitutive |
| PR00131 | GOS9 | |
| PR00133 | chitinase Cht-3 | very weak meristem specific |
| PR00135 | alpha- globulin | Strong in endosperm |
| PR00136 | alanine aminotransferase | Weak in endosperm |

TABLE IV-continued

Alternative rice promoters for use
in the performance of the invention

| PRO # | gene | expression |
|---|---|---|
| PR00138 | Cyclin A2 | |
| PR00139 | Cyclin D2 | |
| PR00140 | Cyclin D3 | |
| PR00141 | Cyclophyllin 2 | Shoot and seed |
| PR00146 | sucrose synthase SS1 (barley) | medium constitutive |
| PR00147 | trypsin inhibitor ITR1 (barley) | weak in endosperm |
| PR00149 | ubiquitine 2 with intron | strong constitutive |
| PR00151 | WSI18 | Embryo and stress |
| PR00156 | HVA22 homologue (putative) | |
| PR00157 | EL2 | |
| PR00169 | aquaporine | medium constitutive in young plants |
| PR00170 | High mobility group protein | Strong constitutive |
| PR00171 | reversibly glycosylated protein RGP1 | weak constitutive |
| PR00173 | cytosolic MDH | shoot |
| PR00175 | RAB21 | Embryo and stress |
| PR00176 | CDPK7 | |
| PR00177 | Cdc2-1 | very weak in meristem |
| PR00197 | sucrose synthase 3 | |
| PRO0198 | OsVP1 | |
| PRO0200 | OSH1 | very weak in young plant meristem |
| PRO0208 | putative chlorophyllase | |
| PRO0210 | OsNRT1 | |
| PRO0211 | EXP3 | |
| PRO0216 | phosphate transporter OjPT1 | |
| PRO0218 | oleosin 18kd | aleurone + embryo |
| PRO0219 | ubiquitine 2 without intron | |
| PRO0220 | RFL | |
| PRO0221 | maize UBI delta intron | not detected |
| PRO0223 | glutelin-1 | |
| PRO0224 | fragment of prolamin RP6 promoter | |
| PRO0225 | 4xABRE | |
| PRO0226 | glutelin OSGLUA3 | |
| PRO0227 | BLZ-2_short (barley) | |
| PR00228 | BLZ-2_long (barley) | |

According to a specific embodiment, the promoter utilized by the present invention is a strong constitutive promoter such that over expression of the construct inserts is effected following transformation. In certain embodiments, the promoter is the *Arabidopsis* Actin 2 (ACT2) promoter (Accession No: U41998, see Table I above).

The nucleic acid construct of some embodiments of the invention can further include an appropriate selectable marker and/or an origin of replication. According to some embodiments of the invention, the nucleic acid construct utilized is a shuttle vector, which can propagate both in *E. coli* (wherein the construct comprises an appropriate selectable marker and origin of replication) and be compatible with propagation in cells. The construct according to the present invention can be, for example, a plasmid, a bacmid, a phagemid, a cosmid, a phage, a virus or an artificial chromosome.

The nucleic acid construct of some embodiments of the invention can be utilized to stably or transiently transform plant cells. In stable transformation, the nucleic acid is integrated into the plant genome and as such it represents a stable and inherited trait. In transient transformation, the exogenous polynucleotide is expressed by the cell transformed but it is not integrated into the genome and as such it represents a transient trait.

Thus, according to some aspects of the present invention, there is provided an isolated cell comprising the nucleic acid construct of the invention.

As used herein, the term "isolated cell" refers to a cell at least partially separated from the natural environment e.g., from a plant. In some embodiments, the isolated cell is a plant cell of a whole plant. In some embodiments, the isolated cell is a plant cell, for example, a plant cell in culture.

The term "plant" as used herein encompasses whole plants, ancestors and progeny of the plants and plant parts, including seeds, shoots, stems, roots (including tubers), and plant cells, tissues and organs. The plant may be in any form including suspension cultures, embryos, meristematic regions, callus tissue, leaves, gametophytes, sporophytes, pollen, and microspores. Plants that are particularly useful in the methods of the invention include all plants which belong to the superfamily Viridiplantae, in particular monocotyledonous and dicotyledonous plants including a fodder or forage legume, ornamental plant, food crop, tree, or shrub selected from the list comprising *Acacia* spp., *Acer* spp., *Actinidia* spp., *Aesculus* spp., *Agathis australis*, *Albizia amara*, *Alsophila tricolor*, *Andropogon* spp., *Arachis* spp, *Areca catechu*, *Astelia fragrans*, *Astragalus cicer*, *Baikiaea plurijuga*, *Betula* spp., *Brassica* spp., *Bruguiera gymnorrhiza*, *Burkea africana*, *Butea frondosa*, *Cadaba farinosa*, *Calliandra* spp, *Camellia sinensis*, *Canna indica*, *Capsicum* spp., *Cassia* spp., *Centroema pubescens*, *Chacoomeles* spp., *Cinnamomum cassia*, *Coffea arabica*, *Colophospermum mopane*, *Coronillia varia*, *Cotoneaster serotina*, *Crataegus* spp., *Cucumis* spp., *Cupressus* spp., *Cyathea dealbata*, *Cydonia oblonga*, *Cryptomeria japonica*, *Cymbopogon* spp., *Cynthea dealbata*, *Cydonia oblonga*, *Dalbergia monetaria*, *Davallia divaricata*, *Desmodium* spp., *Dicksonia squarosa*, *Dibeteropogon amplectens*, *Dioclea* spp, *Dolichos* spp., *Dorycnium rectum*, *Echinochloa pyramidalis*, *Ehraffia* spp., *Eleusine coracana*, *Eragrestis* spp., *Erythrina* spp., *Eucalypfus* spp., *Euclea schimperi*, *Eulalia vi/losa*, *Pagopyrum* spp., *Feijoa sellowlana*, *Fragaria* spp., *Flemingia* spp, *Freycinetia banksli*, *Geranium thunbergii*, *GinAgo biloba*, *Glycine javanica*, *Gliricidia* spp, *Gossypium hirsutum*, *Grevillea* spp., *Guibourtia coleosperma*, *Hedysarum* spp., *Hemaffhia altissima*, *Heteropogon contoffus*, *Hordeum vulgare*, *Hyparrhenia rufa*, *Hypericum erectum*, *Hypeffhelia dissolute*, *Indigo incamata*, *Iris* spp., *Leptarrhena pyrolifolia*, *Lespediza* spp., *Lettuca* spp., *Leucaena leucocephala*, *Loudetia simplex*, *Lotonus bainesli*, *Lotus* spp., *Macrotyloma axillare*, *Malus* spp., *Manihot esculenta*, *Medicago saliva*, *Metasequoia glyptostroboides*, *Musa sapientum*, *Nicotianum* spp., *Onobrychis* spp., *Ornithopus* spp., *Oryza* spp., *Peltophorum africanum*, *Pennisetum* spp., *Persea gratissima*, *Petunia* spp., *Phaseolus* spp., *Phoenix canariensis*, *Phormium cookianum*, *Photinia* spp., *Picea glauca*, *Pinus* spp., *Pisum sativam*, *Podocarpus totara*, *Pogonarthria fleckii*, *Pogonaffhria squarrosa*, *Populus* spp., *Prosopis cineraria*, *Pseudotsuga menziesii*, *Pterolobium stellatum*, *Pyrus communis*, *Quercus* spp., *Rhaphiolepsis umbellata*, *Rhopalostylis sapida*, *Rhus natalensis*, *Ribes grossularia*, *Ribes* spp., *Robinia pseudoacacia*, *Rosa* spp., *Rubus* spp., *Salix* spp., *Schyzachyrium sanguineum*, *Sciadopitys vefficillata*, *Sequoia sempervirens*, *Sequoiadendron giganteum*, *Sorghum bicolor*, *Spinacia* spp., *Sporobolus fimbriatus*, *Stiburus alopecuroides*, *Stylosanthos humilis*, *Tadehagi* spp, *Taxodium distichum*, *Themeda triandra*, *Trifolium* spp., *Triticum* spp., *Tsuga heterophylla*, *Vaccinium* spp., *Vicia* spp., *Vitis vinifera*, *Watsonia pyramidata*, *Zantedeschia aethiopica*, *Zea mays*, amaranth, artichoke, asparagus, broccoli, Brussels sprouts, cabbage, canola, carrot, cauliflower, celery, collard greens, flax, kale, lentil, oilseed rape, okra, onion, potato, rice, soybean, straw, sugar beet, sugar cane, sunflower, tomato, squash tea, maize, wheat, barley, rye, oat, peanut, pea, lentil and alfalfa, cotton, rapeseed, canola, pepper, sunflower, tobacco, eggplant, eucalyptus, a tree, an ornamental plant, a perennial grass and a forage crop. Alternatively algae and other non-Viridiplantae can be used for the methods of the present invention.

According to some embodiments of the invention, the plant or plant cell used by the method of the invention is a crop plant or cell of a crop plant such as rice, maize, wheat, barley, peanut, potato, sesame, olive tree, palm oil, banana, soybean, sunflower, canola, sugarcane, alfalfa, millet, leguminosae (bean, pea), flax, lupinus, rapeseed, tobacco, poplar and cotton.

According to further embodiments the plant cells include tobacco cells, *Agrobacterium rihzogenes* transformed root cell, celery cell, ginger cell, horseradish cell and carrot cells. In one embodiment the tobacco cells are from a tobacco cell line, such as, but not limited to *Nicotiana tabacum* L. cv Bright Yellow (BY-2) cells (Nagata et al, Int Rev Cytol 1992; 132:1-30). The plant cells may be grown according to any type of suitable culturing method, including but not limited to, culture on a solid surface (such as a plastic culturing vessel or plate for example) or in suspension. It will be noted that some cells, such as the BY-2 and carrot cells can be cultured and grown in suspension. Suitable devices and methods for culturing plant cells in suspension are known in the art, for example, as described in International Patent Applications PCT WO98/13469, WO2005/080544 and WO2007/010533. In yet another embodiment the cells are cells of whole tobacco plants or plant tissues, including, but not limited to *Nicotiana benthamiana*.

There are various methods of introducing foreign genes into both monocotyledonous and dicotyledonous plants (Potrykus, I., Annu. Rev. Plant. Physiol., Plant. Mol. Biol. (1991) 42:205-225; Shimamoto et al., Nature (1989) 338: 274-276).

The principle methods of causing stable integration of exogenous DNA into plant genomic DNA include two main approaches:

(i) *Agrobacterium*-mediated gene transfer: Klee et al. (1987) Annu. Rev. Plant Physiol. 38:467-486; Klee and Rogers in Cell Culture and Somatic Cell Genetics of Plants, Vol. 6, Molecular Biology of Plant Nuclear Genes, eds. Schell, J., and Vasil, L. K., Academic Publishers, San Diego, Calif. (1989) p. 2-25; Gatenby, in Plant Biotechnology, eds. Kung, S. and Arntzen, C. J., Butterworth Publishers, Boston, Mass. (1989) p. 93-112.

(ii) Direct DNA uptake: Paszkowski et al., in Cell Culture and Somatic Cell Genetics of Plants, Vol. 6, Molecular Biology of Plant Nuclear Genes eds. Schell, J., and Vasil, L. K., Academic Publishers, San Diego, Calif. (1989) p. 52-68; including methods for direct uptake of DNA into protoplasts, Toriyama, K. et al. (1988) Bio/Technology 6:1072-1074. DNA uptake induced by brief electric shock of plant cells: Zhang et al. Plant Cell Rep. (1988) 7:379-384. Fromm et al. Nature (1986) 319:791-793. DNA injection into plant cells or tissues by particle bombardment, Klein et al. Bio/Technology (1988) 6:559-563; McCabe et al. Bio/Technology (1988) 6:923-926; Sanford, Physiol. Plant. (1990) 79:206-209; by the use of micropipette systems: Neuhaus et al., Theor. Appl. Genet. (1987) 75:30-36; Neuhaus and Spangenberg, Physiol. Plant. (1990) 79:213-217; glass fibers or silicon carbide whisker transformation of cell cultures, embryos or callus tissue, U.S. Pat. No. 5,464,765 or by the direct incubation of DNA with germinating pollen, DeWet et al. in Experimental Manipulation of Ovule Tissue, eds. Chapman, G. P. and Mantell, S. H. and Daniels, W. Longman, London, (1985) p. 197-209; and Ohta, Proc. Natl. Acad. Sci. USA (1986) 83:715-719.

The *Agrobacterium* system includes the use of plasmid vectors that contain defined DNA segments that integrate into the plant genomic DNA. Methods of inoculation of the plant tissue vary depending upon the plant species and the *Agrobacterium* delivery system. A widely used approach is the leaf disc procedure which can be performed with any tissue explant that provides a good source for initiation of whole plant differentiation. See, e.g., Horsch et al. in Plant Molecular Biology Manual A5, Kluwer Academic Publishers, Dordrecht (1988) p. 1-9. Another approach employs the *Agrobacterium* delivery system in combination with vacuum infiltration. The *Agrobacterium* system is especially viable in the creation of transgenic dicotyledonous plants.

There are various methods of direct DNA transfer into plant cells. In electroporation, the protoplasts are briefly exposed to a strong electric field. In microinjection, the DNA is mechanically injected directly into the cells using very small micropipettes. In microparticle bombardment, the DNA is adsorbed on microprojectiles such as magnesium sulfate crystals or tungsten particles, and the microprojectiles are physically accelerated into cells or plant tissues.

Following stable transformation plant propagation is exercised. The most common method of plant propagation is by seed. Regeneration by seed propagation, however, has the deficiency that due to heterozygosity there is a lack of uniformity in the crop, since seeds are produced by plants according to the genetic variances governed by Mendelian rules. Basically, each seed is genetically different and each will grow with its own specific traits. Therefore, it is preferred that the transformed plant be produced such that the regenerated plant has the identical traits and characteristics of the parent transgenic plant. Therefore, it is preferred that the transformed plant be regenerated by micropropagation which provides a rapid, consistent reproduction of the transformed plants.

Micropropagation is a process of growing new generation plants from a single piece of tissue that has been excised from a selected parent plant or cultivar. This process permits the mass reproduction of plants having the preferred tissue expressing the fusion protein. The new generation plants which are produced are genetically identical to, and have all of the characteristics of, the original plant. Micropropagation allows mass production of quality plant material in a short period of time and offers a rapid multiplication of selected cultivars in the preservation of the characteristics of the original transgenic or transformed plant. The advantages of cloning plants are the speed of plant multiplication and the quality and uniformity of plants produced.

Micropropagation is a multi-stage procedure that requires alteration of culture medium or growth conditions between stages. Thus, the micropropagation process involves four basic stages: Stage one, initial tissue culturing; stage two, tissue culture multiplication; stage three, differentiation and plant formation; and stage four, greenhouse culturing and hardening. During stage one, initial tissue culturing, the tissue culture is established and certified contaminant-free. During stage two, the initial tissue culture is multiplied until a sufficient number of tissue samples are produced to meet production goals. During stage three, the tissue samples grown in stage two are divided and grown into individual plantlets. At stage four, the transformed plantlets are transferred to a greenhouse for hardening where the plants' tolerance to light is gradually increased so that it can be grown in the natural environment.

According to some embodiments of the invention, the transgenic plants are generated by transient transformation of leaf cells, meristematic cells or the whole plant.

Transient transformation can be effected by any of the direct DNA transfer methods described above or by viral infection using modified plant viruses.

Viruses that have been shown to be useful for the transformation of plant hosts include CaMV, Tobacco mosaic virus (TMV), brome mosaic virus (BMV) and Bean Common Mosaic Virus (BV or BCMV). Transformation of plants using plant viruses is described in U.S. Pat. No. 4,855,237 (bean golden mosaic virus; BGV), EP-A 67,553 (TMV), Japanese Published Application No. 63-14693 (TMV), EPA 194,809 (BV), EPA 278,667 (BV); and Gluzman, Y. et al., Communications in Molecular Biology: Viral Vectors, Cold Spring Harbor Laboratory, New York, pp. 172-189 (1988). Pseudovirus particles for use in expressing foreign DNA in many hosts, including plants are described in WO 87/06261.

According to some embodiments of the invention, the virus used for transient transformations is avirulent and thus is incapable of causing severe symptoms such as reduced growth rate, mosaic, ring spots, leaf roll, yellowing, streaking, pox formation, tumor formation and pitting. A suitable avirulent virus may be a naturally occurring avirulent virus or an artificially attenuated virus. Virus attenuation may be effected by using methods well known in the art including, but not limited to, sub-lethal heating, chemical treatment or by directed mutagenesis techniques such as described, for example, by Kurihara and Watanabe (Molecular Plant Pathology 4:259-269, 2003), Gal-on et al. (1992), Atreya et al. (1992) and Huet et al. (1994).

Suitable virus strains can be obtained from available sources such as, for example, the American Type culture Collection (ATCC) or by isolation from infected plants. Isolation of viruses from infected plant tissues can be effected by techniques well known in the art such as described, for example by Foster and Tatlor, Eds. "Plant Virology Protocols: From Virus Isolation to Transgenic Resistance (Methods in Molecular Biology (Humana Pr), Vol 81)", Humana Press, 1998. Briefly, tissues of an infected plant believed to contain a high concentration of a suitable virus, preferably young leaves and flower petals, are ground in a buffer solution (e.g., phosphate buffer solution) to produce a virus infected sap which can be used in subsequent inoculations.

Construction of plant RNA viruses for the introduction and expression of non-viral nucleic acid sequences in plants is demonstrated by the above references as well as by Dawson, W. O. et al., Virology (1989) 172:285-292; Takamatsu et al. EMBO J. (1987) 6:307-311; French et al. Science (1986) 231:1294-1297; Takamatsu et al. FEBS Letters (1990) 269:73-76; and U.S. Pat. No. 5,316,931.

When the virus is a DNA virus, suitable modifications can be made to the virus itself. Alternatively, the virus can first be cloned into a bacterial plasmid for ease of constructing the desired viral vector with the foreign DNA. The virus can then be excised from the plasmid. If the virus is a DNA virus, a bacterial origin of replication can be attached to the viral DNA, which is then replicated by the bacteria. Transcription and translation of this DNA will produce the coat protein which will encapsidate the viral DNA. If the virus is an RNA virus, the virus is generally cloned as a cDNA and inserted into a plasmid. The plasmid is then used to make all of the constructions. The RNA virus is then produced by transcribing the viral sequence of the plasmid and translation of the viral genes to produce the coat protein(s) which encapsidate the viral RNA.

In one embodiment, a plant viral polynucleotide is provided in which the native coat protein coding sequence has been deleted from a viral polynucleotide, a non-native plant viral coat protein coding sequence and a non-native promoter, preferably the subgenomic promoter of the non-native coat protein coding sequence, capable of expression in the plant host, packaging of the recombinant plant viral polynucleotide, and ensuring a systemic infection of the host by the recombinant plant viral polynucleotide, has been inserted. Alternatively, the coat protein gene may be inactivated by insertion of the non-native polynucleotide sequence within it, such that a protein is produced. The recombinant plant viral polynucleotide may contain one or more additional non-native subgenomic promoters. Each non-native subgenomic promoter is capable of transcribing or expressing adjacent genes or polynucleotide sequences in the plant host and incapable of recombination with each other and with native subgenomic promoters. Non-native (foreign) polynucleotide sequences may be inserted adjacent the native plant viral subgenomic promoter or the native and a non-native plant viral subgenomic promoters if more than one polynucleotide sequence is included. The non-native polynucleotide sequences are transcribed or expressed in the host plant under control of the subgenomic promoter to produce the desired products.

In a second embodiment, a recombinant plant viral polynucleotide is provided as in the first embodiment except that the native coat protein coding sequence is placed adjacent one of the non-native coat protein subgenomic promoters instead of a non-native coat protein coding sequence.

In a third embodiment, a recombinant plant viral polynucleotide is provided in which the native coat protein gene is adjacent its subgenomic promoter and one or more non-native subgenomic promoters have been inserted into the viral polynucleotide. The inserted non-native subgenomic promoters are capable of transcribing or expressing adjacent genes in a plant host and are incapable of recombination with each other and with native subgenomic promoters. Non-native polynucleotide sequences may be inserted adjacent the non-native subgenomic plant viral promoters such that the sequences are transcribed or expressed in the host plant under control of the subgenomic promoters to produce the desired product.

In a fourth embodiment, a recombinant plant viral polynucleotide is provided as in the third embodiment except that the native coat protein coding sequence is replaced by a non-native coat protein coding sequence.

The viral vectors are encapsidated by the coat proteins encoded by the recombinant plant viral polynucleotide to produce a recombinant plant virus. The recombinant plant viral polynucleotide or recombinant plant virus is used to infect appropriate host plants. The recombinant plant viral polynucleotide is capable of replication in the host, systemic spread in the host, and transcription or expression of foreign gene(s) (exogenous polynucleotide) in the host to produce the desired protein.

Techniques for inoculation of viruses to plants may be found in Foster and Taylor, eds. "Plant Virology Protocols: From Virus Isolation to Transgenic Resistance (Methods in Molecular Biology (Humana Pr), Vol 81)", Humana Press, 1998; Maramorosh and Koprowski, eds. "Methods in Virology" 7 vols, Academic Press, New York 1967-1984; Hill, S. A. "Methods in Plant Virology", Blackwell, Oxford, 1984; Walkey, D. G. A. "Applied Plant Virology", Wiley, New York, 1985; and Kado and Agrawa, eds. "Principles and Techniques in Plant Virology", Van Nostrand-Reinhold, N.Y.

In addition to the above, the polynucleotide of the present invention can also be introduced into a chloroplast genome thereby enabling chloroplast expression.

A technique for introducing exogenous nucleic acid sequences to the genome of the chloroplasts is known. This technique involves the following procedures. First, plant cells are chemically treated so as to reduce the number of chloroplasts per cell to about one. Then, the exogenous polynucleotide is introduced via particle bombardment into the cells with the aim of introducing at least one exogenous polynucleotide molecule into the chloroplasts. The exogenous polynucleotides selected such that it is integratable into the chloroplast's genome via homologous recombination which is readily effected by enzymes inherent to the chloroplast. To this end, the nucleic acid sequence includes, in addition to a gene of interest, at least one polynucleotide stretch which is derived from the chloroplast's genome. In addition, the exogenous polynucleotide includes a selectable marker, which serves by sequential selection procedures to ascertain that all or substantially all of the copies of the chloroplast genomes following such selection will include the exogenous polynucleotide. Further details relating to this technique are found in U.S. Pat. Nos. 4,945,050; and 5,693,507 which are incorporated herein by reference. A polypeptide can thus be produced by the protein expression system of the chloroplast and become integrated into the chloroplast's inner membrane.

According to some embodiments of the invention, the method further comprises growing the plant cell expressing the nucleic acid. The plant cell can be grown as part of a whole plant, or, alternatively, in plant cell culture. In one embodiment, the plant cell is grown in axenic suspension culture, in a bioreactor. Bioreactors suitable for culturing the plant cells suspensions of the invention, and methods for growing the plant cells in suspension are described in detail in, inter alia, U.S. Pat. Nos. 6,391,638 and 7,951,557 and PCTs WO98/13469, WO2005/080544, WO2007/010533, WO2008/135991 and WO2008/132743, all of which are incorporated by reference as if fully set forth herein.

Thus, the invention encompasses plants or plant cultures expressing the nucleic acid sequences, so as to produce the recombinant human α-galactosidase protein of the invention. Once expressed within the plant cell or the entire plant, the level of the human α-galactosidase protein encoded by the nucleic acid sequence can be determined by methods well known in the art such as, activity assays, Western blots using antibodies capable of specifically binding the human α-galactosidase protein, Enzyme-Linked Immuno Sorbent Assay (ELISA), radio-immuno-assays (RIA), immunohistochemistry, immunocytochemistry, immunofluorescence and the like.

Methods of determining the level in the plant of the RNA transcribed from the nucleic acid sequence are well known in the art and include, for example, Northern blot analysis, reverse transcription polymerase chain reaction (RT-PCR) analysis (including quantitative, semi-quantitative or real-time RT-PCR) and RNA-in situ hybridization.

Glycan analysis of the expressed recombinant human α-galactosidase protein of the present invention indicates that the polypeptide is glycosylated in the plant cell, resulting in a recombinant human α-galactosidase protein having exposed mannose and plant specific glycan residues (see Example IV below). Thus, according to some embodiments of the invention, cells expressing the expression vector of the invention produce a human α-galactosidase protein having at least one, optionally at least two, optionally at least three or optionally at least four or more core β-(1,2) xylose residues. In yet other embodiments the cells expressing the expression vector of the invention produce a human α-galactosidase protein having at least one, optionally at least two, optionally at least three or optionally at least four or more core α-(1,3) fucose residues. In other embodiments the cells expressing the expression vector of the invention produce a human α-galactosidase protein having at least one, optionally at least two, optionally at least three or optionally at least four or more terminal β(1-2)N acetylglucosamine. In other embodiments the cells expressing the expression vector of the invention produce a human α-galactosidase protein having at least one, optionally at least two, optionally at least three or optionally at least four or more exposed mannose residues. In one particular embodiment the cells expressing the expression vector of the invention produce a human α-galactosidase protein having nine mannose residues (M9), at least one, optionally at least two, optionally at least three of them being exposed mannose residues. In one embodiment the cells expressing the expression vector of the invention produces a human α-galactosidase protein having at least one exposed mannose residue, at least one core β-(1,2) xylose residue and at least one α-(1,3) fucose residue.

Yet further, according to some embodiments of the invention, there is provided a composition comprising a plurality of human α-galactosidase protein molecules produced by cells expressing the expression vector of the invention, wherein the most predominant glycan structures of the plurality of human α-galactosidase protein molecules are mannose 3-β-(1,2) xylose-α-(1,3) fucose [Fc(3)M3X] and/or mannose 4-β-(1,2) xylose (M4X); and mannose 8 (M8). In some embodiments of the invention, the glycan structures mannose 3-β-(1,2) xylose-α-(1,3) fucose [Fc(3)M3X] and/or mannose 4-β-(1,2) xylose (M4X) comprise about 20%, about 25%, about 30%, about 35% or about 40%, about 45%, about 50%, about 55%, about 60%, about 70%, about 80% of the profile of human α-galactosidase protein molecules in the plurality, and the glycan structure mannose 8 (M8) comprises 20%, about 25%, about 30%, about 35% or about 40%, about 45%, about 50%, about 55%, about 60%, about 70%, about 80% of the profile of the human α-galactosidase protein molecules in the plurality.

In yet further embodiments of the present invention, the composition comprises a plurality of human α-galactosidase protein molecules produced by cells expressing the expression vector of the invention, wherein said plurality of human α-galactosidase protein molecules comprise at least about 0.5%, at least about 0.6%, about 0.7%, about 0.8%, about 0.9%, about 1.0%, about 1.1%, about 1.2%, about 1.3%, about 1.4%, about 1.5%, about 1.75%, about 2.0%, about 2.5%, about 3.0%, about 3.5%, about 4.0%, about 4.5%, about 5.0% or more human α-galactosidase protein molecules having glycan structures of nine mannose residues, at least one, optionally at least two, optionally at least three of them being exposed mannose residues.

The human α-galactosidase protein produced by cells expressing the expression vector of the invention was shown to have α-galactosidase catalytic activity identical to that of native human α-galactosidase enzyme. Exposure of the recombinant α-galactosidase of the invention to conditions simulating an in-vivo environment of the enzyme when administered for enzyme replacement therapy further indicate that the human α-galactosidase protein produced by cells expressing the expression vector of the invention could possess pharmacokinetics similar to those of mammalian-cell expressed recombinant human α-galactosidase (Replagal®) (see Example 3 and FIGS. 2 and 3 herein).

Thus, the human α-galactosidase protein produced by cells expressing the expression vector of the invention can be used to produce a pharmaceutical composition. The pharmaceutical composition can be used for treatment or prevention of Fabry disease in a subject in need thereof. In some embodiments, cells expressing the human α-galactosidase protein can be used for treatment or prevention of Fabry disease in a subject in need thereof. Methods for preparation and administration of plant cells recombinantly expressing human proteins are known in the art, for example, PCT WO2007/010533 to Shaaltiel et al.

Thus, according to another aspect of the present invention there is provided a pharmaceutical composition which includes, as an active ingredient thereof, a human α-galactosidase protein translationally fused at the C-terminal to an endoplasmic reticulum retention signal peptide, and a pharmaceutical acceptable carrier. In some embodiments of the present invention, the human α-galactosidase protein has an N-terminal Glycine residue. In some embodiments of the present invention, the human α-galactosidase protein has an amino acid sequence as set forth in SEQ ID NO: 16. In some embodiments, the human α-galactosidase protein translationally fused at the C-terminal to an endoplasmic reticulum retention signal peptide has an amino acid as set forth in SEQ ID NO: 21.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the recombinant human α-galactosidase protein accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

Conventional approaches for drug delivery to the central nervous system (CNS) include: neurosurgical strategies (e.g., intracerebral injection or intracerebroventricular infusion); molecular manipulation of the agent (e.g., production of a chimeric fusion protein that comprises a transport peptide that has an affinity for an endothelial cell surface molecule in combination with an agent that is itself incapable of crossing the BBB) in an attempt to exploit one of the endogenous transport pathways of the BBB; pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide). However, each of these strategies has limitations, such as the inherent risks associated with an invasive surgical procedure, a size limitation imposed by a limitation inherent in the endogenous transport systems, potentially undesirable biological side effects associated with the systemic administration of a chimeric molecule comprised of a carrier motif that could be active outside of the CNS, and the possible risk of brain damage within regions of the brain where the BBB is disrupted, which renders it a suboptimal delivery method.

Alternately, one may administer the pharmaceutical composition in a local rather than systemic manner, for example, via injection of the pharmaceutical composition directly into a tissue region of a patient.

The term "tissue" refers to part of an organism consisting of cells designed to perform a function or functions. Examples include, but are not limited to, brain tissue, retina, skin tissue, hepatic tissue, pancreatic tissue, bone, cartilage, connective tissue, blood tissue, muscle tissue, cardiac tissue brain tissue, vascular tissue, renal tissue, pulmonary tissue, gonadal tissue, hematopoietic tissue.

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with some embodiments of the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the active ingredients can be optionally formulated through administration of the whole cells producing a human α-galactosidase protein according to the present invention. The active ingredients can also optionally be formulated by combining the active ingredients and/or the cells with pharmaceutically acceptable carriers well known in the art, producing pharmaceutical compositions. Such carriers enable the cells and/or pharmaceutical composition to be formulated as tablets, pills, dragees, capsules, liquids, gels, syrups, slurries, suspensions, and the like, for oral ingestion by a patient. When used for oral administration, whole cells, or fractions of cells can be use fresh or processed (e.g. lyophilized, frozen, dried, etc).

Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to some embodiments of the invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of some embodiments of the invention may also be formulated in rectal compositions such as suppositories or retention enemas, using, e.g., conventional suppository bases such as cocoa butter or other glycerides.

Pharmaceutical compositions suitable for use in context of some embodiments of the invention include compositions wherein the active ingredients are contained in an amount effective to achieve the intended purpose. More specifically, a therapeutically effective amount means an amount of active ingredients ($\alpha$-galactosidase) effective to prevent, alleviate or ameliorate symptoms of a disorder (e.g., Fabry's disease) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide serum and cell levels of the active ingredient which are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of some embodiments of the invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

The pharmaceutical composition can be used for treatment or prevention of Fabry disease in a subject in need thereof. Thus, according to another aspect of the present invention there is provided a method for treating or preventing Fabry disease in a subject in need thereof, the method comprising administering to the subject an effective amount of a pharmaceutical composition which includes, as an active ingredient thereof, a human α-galactosidase protein translationally fused at the C-terminal to an endoplasmic reticulum retention signal peptide, and a pharmaceutical acceptable carrier. In some embodiments of the present invention, the human α-galactosidase protein has an N-terminal Glycine residue. In other embodiments, the human α-galactosidase protein has an amino acid sequence as set forth in SEQ ID NO: 16.

The term "treating" refers to inhibiting, preventing or arresting the development of a pathology (disease, disorder or condition) and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology.

As used herein, the term "preventing" refers to keeping a disease, disorder or condition from occurring in a subject who may be at risk for the disease, but has not yet been diagnosed as having the disease.

As used herein, the term "subject" includes mammals, preferably human beings at any age which suffer from the pathology. Preferably, this term encompasses individuals who are at risk to develop the pathology.

As used herein the phrase "treatment regimen" refers to a treatment plan that specifies the type of treatment, dosage, schedule and/or duration of a treatment provided to a subject in need thereof (e.g., a subject diagnosed with a pathology). The selected treatment regimen can be an aggressive one which is expected to result in the best clinical outcome (e.g., complete cure of the pathology) or a more moderate one which may relief symptoms of the pathology yet results in incomplete cure of the pathology. It will be appreciated that in certain cases the more aggressive treatment regimen may be associated with some discomfort to the subject or adverse side effects (e.g., a damage to healthy cells or tissue). The type of treatment can include a surgical intervention (e.g., removal of lesion, diseased cells, tissue, or organ), a cell replacement therapy, an administration of a therapeutic drug (e.g., receptor agonists, antagonists, hormones, chemotherapy agents) in a local or a systemic mode, an exposure to radiation therapy using an external source (e.g., external beam) and/or an internal source (e.g., brachytherapy) and/or any combination thereof. The dosage, schedule and duration of treatment can vary, depending on the severity of pathology and the selected type of treatment, and those of skills in the art are capable of adjusting the type of treatment with the dosage, schedule and duration of treatment.

It is expected that during the life of a patent maturing from this application many relevant vectors, promoter elements, plant cells and carriers will be developed and the scope of the terms provided herein is intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W.H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1, 2, 317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example I

Construction of the Plant α-Galactosidase Expression Construct cDNA encoding the human α-galactosidase protein (EC 3.2.1-22 GenBank: X05790) was optimized and synthesized by GENEART AG (Regensburg, Germany). The codon usage without the leader peptide (endoplasmic reticulum target signal peptide) was adapted to the codon bias of *Nicotiana tabacum* genes. During the optimization process the following cis-acting sequence motifs were avoided: Internal TATA-boxes, chi-sites and ribosomal entry sites, AT-rich or GC-rich sequence stretches, RNA instability elements ("killer motifs"), Repeat sequences and RNA secondary structures, splice donor (cryptic) and acceptor sites, branch points. In addition, regions of very high (>80%) or very low (<30%) GC content has been avoided.

The nucleotide sequence of the native human α-galactosidase leader peptide (endoplasmic reticulum target signal peptide) (FIG. 1, first 31 amino acids in red) of full length human α-galactosidase protein (GenBank: X05790) was replaced with a nucleotide sequence encoding the 33 amino acid endoplasmic reticulum targeting signal peptide (leader peptide) of the *Arabidopsis* ABPI protein (marked in green in FIG. 1, SEQ ID NO: 4). This signal peptide provides efficient targeting of α-galactosidase to the secretory pathway and is cleaved from the polypeptide, by signal peptidase, once the protein has been translocated into the endoplasmic reticulum. A nucleotide sequence (SEQ ID NO: 19) encoding the endoplasmic reticulum retention signal SEKDEL (SEQ ID NO: 6) was added to the cDNA sequence at the 3' terminus, allowing retrieval of the expressed protein from the Golgi apparatus, effectively maintaining the protein in the endoplasmic reticulum. SEQ ID NO: 2 represents the complete coding sequence of the expressed recombinant human α-galactosidase (SEQ ID NO: 1), including the N-terminal ABPI endoplasmic reticulum targeting signal peptide, human α-galactosidase protein and the SEKDEL endoplasmic reticulum retention signal.

Example II

Expression of Recombinant Human α-Galactosidase in Plants

Transient Expression System in *N. benthamiana*

The use of plant viral vectors was chosen in this case as an alternative to transgenic plants, allowing for the rapid, high level transient expression of proteins in mature whole plants.

The protein of interest was expressed from a strong subgenomic viral coat protein promoter. The system relies on transient amplification (by agroinfection) of viral vectors delivered to a plant by *Agrobacterium*, in which the plant functional promoter and the cDNA encoding a viral replicon are transferred as T-DNA from *agrobacterium* into plant cells. The T-DNA is transcribed in-planta by the plant promoter to generate biologically active viral RNA that initiates self replication.

For the transient expression a 3 vector recombination system based on the system previously developed as described (Gleba et al., Vaccine 23 2042-2048, 2005) was employed. α-galactosidase cDNA was inserted into one of the vectors, and the two other vectors containing genes for construction of the whole viral replicon (RdRp and Integrase), thus generating a biologically active viral RNA capable of initiating self replication.

Transfection of Whole Plants—

*N. Benthamiana* plants were germinated and grown in commercial mix soil (Givaat Ada, Ill.) supplemented with granular slow release fertilizer (Scott Marysville, Ohio) under a long day (16 h light/8 h dark) light regime at 24° C.-25° C.

*Agrobacteria* were transformed with the pICH20866-alpha-GAL based replicon vector system using electroporation (2500V, 5 msec) [den Dulk-Ra, A. and Hooykaas, P. J. (1995) Methods Mol. Biol. 55:63-72]. Plants were infiltrated with *Agrobacteria* containing the 3 ICON plasmids by vacuum infiltration with standard methods known in the art. Briefly, *N. benthamiana* plants, 5-6 week old were infiltrated by immersing all aerial plant organs into a bacterial suspension and were placed in a vacuum chamber. A minus (−) 0.8 bar vacuum was applied for 1 minute, followed by a quick return to atmospheric pressure. Plants were returned to the greenhouse for additional 5-7 days under the same growth conditions.

Tobacco Plant Extract:

Samples of *Nicotiana benthamiana* leaves were harvested 5 days post infiltration and extracted in Laemmli buffer for SDS-PAGE, or in activity assay buffer (20 mM citric acid, 30 mM sodium phosphate, 0.1% BSA and 0.67% ethanol, pH 4.6.) for assay of catalytic activity of the plant expressed protein.

Tobacco Plant Extract Purification:

Human α-galactosidase protein from plant extracts was purified by a two-step ammonium sulfate differential precipitation ("salting out": $1^{st}$ step 0.57M; $2^{nd}$ step 2.27M), followed by hydrophobic interaction chromatography (Phenyl 650 M resin) and cation exchange chromatography.

Stable Expression in *N. tobaccum* BY2 Cells

*Agrobacterium* mediated transformation is widely used to introduce foreign genes into a plant cell genome. This technique is based on the natural capability of the *agrobacterium* to transform plant cells by transferring a plasmid DNA segment, the transferred DNA (T-DNA), into the host cell genome. Using this approach, a T-DNA molecule, consisting of a foreign gene and its regulatory elements, is randomly introduced into the plant genome. The site of integration, as well as the copy number of the gene insertions is not controlled, thus the transformation process results in a 'pool' of transgenic cells composed of cells with various levels of expression of the transgene. The transgenic 'pool' is subsequently used for clone isolation. Clone isolation results in the establishment of many single cell lines, from which the clone with the highest expression level of the foreign gene is then selected.

BY2 suspension culture was co-cultivated, for 48 hours, with the *Agrobacterium tumefactions* EHA105 strain carrying the vector harboring the α-GAL gene and the neomycin phosphotransferase (NPTII) selection gene.

Subsequently, the cells were kept in media supplemented with 50 mg/L of Kanamaycin and 250 mg/L Cefotaxime. The NPTII gene confers resistance to Kanamycin, thus only NPTII positive BY2 cells survive in this selection media. The Cefotaxime was used to selectively kill the *agrobacterium*, the plant cells being resistant to this antibiotic. Once a nicely growing transgenic cell suspension was established, it was used for screening and isolating individual cell lines. To allow for the selection of individual cell lines, aliquots of highly diluted cell suspension were spread on solid BY-2 medium. The cells were then grown until small calli developed. Each callus was then re-suspended in liquid culture. The cells were then sampled and the samples were evaluated for α-GAL levels. The lines that expressed relatively high α-GAL activity levels were then further re-analyzed and compared for α-GAL levels ending with the final selection of candidate α-GAL expressing lines.

Tobacco Cell Extract:

100 mg of transformed BY2 cells expressing the human α-galactosidase protein were homogenized for 5 min in 200 ul 20 mM phosphate buffer 0.5M containing 20 mM EDTA 2 mM DTT and 2 mM PMSF, pH=7.2. The homogenate was centrifuged and the supernatant containing the recombinant human α-galactosidase protein was collected [crude extract]—. α-galactosidase catalytic activity in crude was determined by PNP-G assay.

PNP-G Assay

α-galactosidase galactoside hydrolase activity was determined using p-nitrophenylalpha-D-galactopyranoside (pNP-alpha-D-Gal, GBB1290, IRIS Biotech, Germany) as a hydrolysis substrate. The assay buffer contained 20 mM citric acid, 30 mM sodium phosphate, 0.1% BSA and 0.67% ethanol at pH 4.6. Samples (50 µl) were incubated with 150 µl assay buffer. The substrate (pNP-alpha-D-Gal) was added (30 µL) to a final concentration of 8 mM p-NP-alpha-D Gal. The reaction mixture was incubated at 37° C. for 90 minutes. After 90 minutes, the reaction was quenched by the addition of 100 µl sodium carbonate (2M) to each well, in order to terminate the reaction and enable the generation of the p-nitrophenolate chromophore. Results were calculated from Absorbance at 405 nm was measured.

Modification of the Plant-Expressed Human α-Galactosidase:

Sequencing of the protein product from the transformed plants revealed that, in some instances, upon cleavage of the ABPI signal, the recombinant human α-galactosidase protein retains the last amino acid Glycine of the signal peptide at the N terminus of the mature α-galactosidase protein. Thus, the recombinant human α-galactosidase protein can be either without the Glycine of the signal peptide at the N-terminus (e.g. SEQ ID NO: 20, coding sequence as in SEQ ID NO: 22) or including a Glycine at the N-terminus (e.g. SEQ ID NO: 21, coding sequence as in SEQ ID NO: 23).

Glycan Analysis of the Plant-Expressed Human α-Galactosidase:

Samples of recombinant human α-galactosidase protein product from the transformed plants were reduced, alkylated with DTT and iodoacetamide, and separated on a 12.5% SDS-PAGE. Bands corresponding to the correct molecular weight were excised, protein extracted, and subjected to glycan analysis consisting of trypsin digestion followed by both PNGase A and PNGase F digestion. PNGase A digestion releases all the N-linked glycans and PNGase F release all glycans except those containing α 1-3 core fucose.

The free glycans were extracted, purified and then labeled with the fluorescent reagent anthranilamide (2AB) followed by removal of excess 2AB.

Glycans were separated using a TSK gel Amide 80 normal phase HPLC and detected using a fluorescence detector. A Dextran hydrolysate served as a ladder for calculation of glucose unit (GU) values. Glycan profile is constructed by calculating the relative peak areas from the chromatogram of the PNGase A digestion. Assignment of the glycans is established by calculation of the GU values of the peaks found in both endoglycoside digestions and based on additional various exoglycoside digestions.

Results:

Comparing between different α-galactosidase constructs, it was uncovered that the addition of an ABPI endoplasmic reticulum targeting signal peptide (SEQ ID NO: 4) to the human recombinant α-galactosidase polypeptide improved expression of the recombinant protein in transiently expressing *N. benthamiana* plants (FIG. 2, lane 2), compared to α-galactosidase sequences expressed with an apple pectinase endoplasmic reticulum targeting signal peptide (apple pectinase ER targeting signal peptide as encoded by SEQ ID NO: 10) α-galactosidase-apple pectinase ER signal peptide-protein as encoded by SEQ ID NO: 8 or SEQ ID NO: 11), or α-galactosidase protein expressed with an endochitinase B endoplasmic reticulum targeting signal peptide (endochitinase signal protein, SEQ ID NO: 14, as encoded by SEQ ID NO: 15). Assay of the catalytic activity (see above) confirmed that increased protein seen in FIG. 2 is reflected in concomitant increase in enzymatic activity (FIG. 3, column B) per kg leaves, compared with α-galactosidase sequences expressed with an apple pectinase endoplasmic reticulum targeting signal peptide or α-galactosidase protein expressed with an endochitinase B endoplasmic reticulum targeting signal peptide (endochitinase signal protein, SEQ ID NO: 14, as encoded by SEQ ID NO: 15).

Glycan analysis of the recombinant human α-galactosidase protein product from the transformed tobacco cells expressing a human α-galactosidase protein with the addition of an ABPI endoplasmic reticulum targeting signal peptide (e.g. SEQ ID NO: 1, encoded by SEQ ID NO: 2) revealed a glycan profile comprising main glycan structures of high mannose glycan structures (e.g. 3 to 6, 7, 8 or 9 mannose residues, with terminal, exposed mannose), and characteristic plant-specific glycans, such as β-(1,2) xylose and α-(1,3) fucose (FIG. 7). Predominant glycan structures representing a high percentage of the glycan profile included about 30% having mannose 3-β-(1,2) xylose-α-(1,3) fucose [Fc(3)M3X] and/or mannose 4-α-(1,2) xylose (M4X); and another about 30% mannose 8 (M8) glycans (FIG. 8). FIG. 8 is an illustrated table showing the distribution of the glycan structures within the protein samples from the transformed cells. A-Gal A and A-Gal-B are two representative analyses of the recombinant human α-galactosidase protein product from the transformed plant cells.

Glycan structures can be further categorized according to the sugar residues present in the complex glycans. Table V below details the distribution of glycan structures in the human α-galactosidase protein product from transformed plants, according to specific sugars:

TABLE V

Saccharide content of glycans

| GLYCAN TYPE | % OF TOTAL GLYCANS |
|---|---|
| Fucose containing glycans | ~35 |
| Xylose containing glycans | ~50 |
| High mannose | ~60 |
| N-acetylglucosamine containing glycans | ~10 |

Thus, the human α-galactosidase protein product expressed in tobacco cell culture from the construct comprising SEQ ID NO: 2 was characterized by significant percentage of plant specific glycan structures (having fucose and xylose components), and high mannose glycosylation.

Example III

Stability of Plant Expressed Human Recombinant A-Galactosidease Under In-Vivo Conditions In order to approximate pharmacokinetics of the plant expressed human recombinant α-galactosidase, recombinant enzyme preparations were exposed to simulated in-vivo conditions and catalytic activity monitored.

Stability in Plasma:

Stability of enzymatic activity in plasma was assessed by adding recombinant plant extract or α-galactosidase purified from plant extract to human plasma to a final concentration of 1 μg/ml (e.g. 10 μl extract or purified α-galactosidase to 190 μl human plasma), incubating at 37° C., and following the α-galactosidase catalytic activity in samples at set intervals over an hour's time.

Comparison between α-galactosidase from *N. benthamaina* plants transformed with SEQ ID NO: 11, encoding an α-galactosidase with an apple pectinase endoplasmic reticulum targeting signal peptide (SEQ ID NO: 12) and α-galactosidase from *N. benthamaina* plants transformed with SEQ ID NO: 2, encoding α-galactosidase with an ABPI endoplasmic reticulum targeting signal peptide (SEQ ID NO: 1) (FIG. 4) indicates a clear advantage of the *N. benthamiana*-expressed α-galactosidase from the construct having an ABPI endoplasmic reticulum targeting signal peptide (FIG. 4, closed or solid squares), as compared to recombinant α-galactosidase expressed from the construct with an apple pectinase endoplasmic reticulum targeting signal leader (FIG. 4, open squares).

Comparison between α-galactosidase expressed in *N. tabacuum* plant cells (BY2) transformed with SEQ ID NO: 2, encoding an α-galactosidase protein with an ABPI endoplasmic reticulum targeting signal peptide (SEQ ID NO: 1), resulting in a mature recombinant α-galactosidase protein as set forth in SEQ ID NO: 21 with α-galactosidase expressed in mammalian cells (REPLAGAL™) revealed similar stability of the enzymatic activity when incubated for one hour at 37° C. in plasma (FIG. 5), and when incubated over 9 days under lysosome-like conditions (pH=4.6 and 37° C., FIG. 6). This similarity under simulated in-vivo conditions suggests that the plant cell expressed recombinant α-galactosidase would have pharmacokinetics comparable to those of the mammalian cell-expressed, clinically approved enzyme (REPLAGAL™).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A nucleic acid expression construct, the construct comprising a nucleic acid sequence encoding a human α-galactosidase protein, wherein said human α-galactosidase protein is translationally fused at the N-terminal to an *Arabidopsis* ABPI endoplasmic reticulum targeting signal peptide and wherein said human α-galactosidase protein is translationally fused at the C-terminal to an endoplasmic reticulum retention signal peptide, and wherein said nucleic acid sequence is codon-optimized for plant expression.

2. The nucleic acid construct of claim 1, wherein said nucleic acid sequence comprises SEQ ID NO: 22.

3. The nucleic acid construct of claim 1, wherein said *Arabidopsis* ABPI endoplasmic reticulum target signal peptide is as set forth in SEQ ID NO: 4.

4. The nucleic acid construct of claim 1, comprising a nucleic acid sequence encoding said endoplasmic reticulum targeting signal peptide as set forth in SEQ ID NO: 5.

5. The nucleic acid construct of claim 1, wherein said endoplasmic reticulum retention signal peptide is as set forth in SEQ ID NO: 6.

6. The nucleic acid construct of claim 1, comprising a nucleic acid sequence encoding said endoplasmic reticulum retention peptide as set forth in SEQ NO: 19.

7. The nucleic acid construct of claim 1, wherein said nucleic acid sequence has a sequence as set forth in SEQ ID NO: 2.

8. The nucleic acid construct of claim 1, wherein said human α-galactosidase protein has an amino acid sequence as set forth in SEQ ID NO: 1.

9. An isolated plant cell comprising the nucleic acid construct of claim 1.

10. The cell of claim 9, wherein said plant cell is a tobacco cell.

11. The cell of claim 10, wherein said tobacco cell is a BY-2 cell.

12. A method of producing a catalytically active recombinant human α-galactosidase protein, comprising:
providing a cell according to claim 9; and
growing said cell so as to produce said catalytically active recombinant human α-galactosidase protein; and
isolating said catalytically active recombinant human α-galactosidase protein from said cell, wherein said catalytic activity is hydrolysis of p-nitrophenylalpha-D-galactopyranoside.

13. The method of claim 12, wherein said cell is an isolated cell cultured in a cell culture medium.

14. The method of claim 13, wherein said culturing is affected in a disposable bioreactor.

15. A human α-galactosidase protein having an N-terminal Glycine residue, wherein said human α-galactosidase protein is translationally fused at the C-terminal to an endoplasmic reticulum retention signal peptide and wherein said human α-galactosidase protein is catalytically active as determined by p-nitrophenylalpha-D-galactopyranoside assay.

16. The human α-galactosidase protein of claim 15, having an amino acid sequence as set forth in SEQ ID NO: 16.

17. A pharmaceutical composition comprising, as an active ingredient, the human α-galactosidase protein of claim 15 and a pharmaceutically acceptable carrier.

18. A pharmaceutical composition comprising the human α-galactosidase protein of claim 15, having a glycan structure comprising nine mannose residues, wherein three are exposed mannose residues, and a pharmaceutically acceptable carrier.

19. A pharmaceutical composition comprising, as an active ingredient, a population of human α-galactosidase proteins of claim 15, wherein at least 0.5% of said population has a glycan structure comprising nine mannose residues, wherein three are exposed mannose residues.

20. A pharmaceutical composition comprising, as an active ingredient, a population of human α-galactosidase proteins of claim 15, wherein the predominant glycan structures of said population of human α-galactosidase proteins are mannose 4-β-(1,2) xylose (M4X); mannose 3-β-(1,2) xylose-α-(1,3) fucose [Fc(3)M3X]; and mannose 8 (M8), and a pharmaceutically acceptable carrier.

21. A pharmaceutical composition comprising, as an active ingredient, the cell of claim 9 and a pharmaceutically acceptable carrier.

22. A method of treating Fabry's disease in a subject in need thereof, comprising administering to the subject the pharmaceutical composition of claim 17.

23. A method of treating Fabry's disease in a subject in need thereof, comprising administering to the subject the pharmaceutical composition of claim 20.

24. A method of treating Fabry's disease in a subject in need thereof, comprising administering to the subject the pharmaceutical composition of claim 21.

* * * * *

SEQUENCE LISTING

<160> NUMBER OF SEQ ID NOS: 23

<210> SEQ ID NO 1
<211> LENGTH: 437
<212> TYPE: PRT
<213> ORGANISM: Artificial sequence
<220> FEATURE:
<223> OTHER INFORMATION: Recombinant Alpha-Gal fused with ABPI and an ER
      signal peptide (ABPI+AGAL+SEKDEL)

<400> SEQUENCE: 1

```
Met Ile Val Leu Ser Val Gly Ser Ala Ser Ser Pro Ile Val Val
1               5                   10                  15

Val Phe Ser Val Ala Leu Leu Leu Phe Tyr Phe Ser Glu Thr Ser Leu
                20                  25                  30

Gly Leu Asp Asn Gly Leu Ala Arg Thr Pro Thr Met Gly Trp Leu His
                35                  40                  45

Trp Glu Arg Phe Met Cys Asn Leu Asp Cys Gln Glu Glu Pro Asp Ser
    50                  55                  60

Cys Ile Ser Glu Lys Leu Phe Met Glu Met Ala Glu Leu Met Val Ser
65                  70                  75                  80

Glu Gly Trp Lys Asp Ala Gly Tyr Glu Tyr Leu Cys Ile Asp Asp Cys
                85                  90                  95

Trp Met Ala Pro Gln Arg Asp Ser Glu Gly Arg Leu Gln Ala Asp Pro
                100                 105                 110

Gln Arg Phe Pro His Gly Ile Arg Gln Leu Ala Asn Tyr Val His Ser
                115                 120                 125

Lys Gly Leu Lys Leu Gly Ile Tyr Ala Asp Val Gly Asn Lys Thr Cys
                130                 135                 140

Ala Gly Phe Pro Gly Ser Phe Gly Tyr Tyr Asp Ile Asp Ala Gln Thr
145                 150                 155                 160

Phe Ala Asp Trp Gly Val Asp Leu Leu Lys Phe Asp Gly Cys Tyr Cys
                165                 170                 175

Asp Ser Leu Glu Asn Leu Ala Asp Gly Tyr Lys His Met Ser Leu Ala
                180                 185                 190

Leu Asn Arg Thr Gly Arg Ser Ile Val Tyr Ser Cys Glu Trp Pro Leu
                195                 200                 205

Tyr Met Trp Pro Phe Gln Lys Pro Asn Tyr Thr Glu Ile Arg Gln Tyr
                210                 215                 220

Cys Asn His Trp Arg Asn Phe Ala Asp Ile Asp Asp Ser Trp Lys Ser
225                 230                 235                 240

Ile Lys Ser Ile Leu Asp Trp Thr Ser Phe Asn Gln Glu Arg Ile Val
                245                 250                 255

Asp Val Ala Gly Pro Gly Gly Trp Asn Asp Pro Asp Met Leu Val Ile
                260                 265                 270

Gly Asn Phe Gly Leu Ser Trp Asn Gln Gln Val Thr Gln Met Ala Leu
                275                 280                 285

Trp Ala Ile Met Ala Ala Pro Leu Phe Met Ser Asn Asp Leu Arg His
                290                 295                 300

Ile Ser Pro Gln Ala Lys Ala Leu Leu Gln Asp Lys Asp Val Ile Ala
305                 310                 315                 320

Ile Asn Gln Asp Pro Leu Gly Lys Gln Gly Tyr Gln Leu Arg Gln Gly
                325                 330                 335

Asp Asn Phe Glu Val Trp Glu Arg Pro Leu Ser Gly Leu Ala Trp Ala
                340                 345                 350
```

```
Val Ala Met Ile Asn Arg Gln Glu Ile Gly Gly Pro Arg Ser Tyr Thr
            355                 360                 365

Ile Ala Val Ala Ser Leu Gly Lys Gly Val Ala Cys Asn Pro Ala Cys
    370                 375                 380

Phe Ile Thr Gln Leu Leu Pro Val Lys Arg Lys Leu Gly Phe Tyr Glu
385                 390                 395                 400

Trp Thr Ser Arg Leu Arg Ser His Ile Asn Pro Thr Gly Thr Val Leu
                405                 410                 415

Leu Gln Leu Glu Asn Thr Met Gln Met Ser Leu Lys Asp Leu Leu Ser
            420                 425                 430

Glu Lys Asp Glu Leu
        435

<210> SEQ ID NO 2
<211> LENGTH: 1311
<212> TYPE: DNA
<213> ORGANISM: Artificial sequence
<220> FEATURE:
<223> OTHER INFORMATION: Coding sequence of recombinant Alpha-Gal fused
      to ABPI and an ER signal peptide (ABPI+AGAL+SEKDEL)

<400> SEQUENCE: 2
atgattgtgc tttctgtggg atctgcttct tcttctccaa ttgtggtggt gttctctgtg      60
gctcttcttc ttttctactt ctctgagact tctcttggcc ttgataatgg acttgctagg     120
actccaacta tgggatggct tcattgggaa cgtttcatgt gcaatctcga ttgtcaagag     180
gaaccagatt cttgcatttc cgagaagctt tcatggaaa tggctgagct tatggtttct     240
gagggatgga aggatgctgg atatgagtac ctctgcatcg atgattgctg gatggctcca     300
caaagagatt ctgagggaag gcttcaagct gatccacaaa ggttcccaca tggaattagg     360
caactcgcta actacgttca ctctaaggga cttaagcttg aatctacgc tgatgtggga     420 aacaagactt gtgctggatt tccaggatct ttcggttact acgatatcga tgctcagact     480
tttgctgatt ggggagtgga tcttcttaag ttcgatggat gctactgtga ttctcttgag     540
aacctcgctg atggttataa gcacatgtct ctcgctctta atagaactgg acgttccatt     600
gtgtattctt gcgagtggcc actttacatg tggccattcc agaagccaaa ctacactgag     660
attaggcaat actgcaacca ttggaggaac ttcgctgata ttgatgattc ctggaagtct     720
atcaagtcca tccttgattg gacttcattc aatcaagaac gtattgtgga tgttgctgga     780
cctggtggat ggaatgatcc agatatgctc gtgattggaa actttggact tcttggaac    840 cagcaagtta ctcaaatggc tctctgggct attatggctg ctccactctt catgtctaac     900
gatcttaggc acatttctcc acaagctaag ctttgctcc aggataagga tgtgattgct      960
atcaaccagg atccacttgg aaagcaagga taccaactta ggcagggtga ttattttgag    1020
gtttgggaga ggccactttc tggacttgct tgggctgttg ctatgattaa caggcaagag    1080
attggaggac caaggtctta cactattgct gtggcttctc ttggaaaggg tgttgcttgt    1140
aatccagctt gcttcattac tcagcttttg ccagtgaaga ggaagcttgg atttttacgag   1200 tggacttcta ggcttaggtc acacattaac ccaactggaa ctgtgcttct tcagctcgag    1260
aacactatgc agatgtctct taaggatttg ctctccgaga aggatgagct t              1311

<210> SEQ ID NO 3
<211> LENGTH: 31
<212> TYPE: PRT
<213> ORGANISM: Artificial sequence
<220> FEATURE:
```

<223> OTHER INFORMATION: Human A-Gal leader sequence

<400> SEQUENCE: 3

Met Gln Leu Arg Asn Pro Glu Leu His Leu Gly Cys Ala Leu Ala Leu
1               5                   10                  15

Arg Phe Leu Ala Leu Val Ser Trp Asp Ile Pro Gly Ala Arg Ala
            20                  25                  30

<210> SEQ ID NO 4
<211> LENGTH: 33
<212> TYPE: PRT
<213> ORGANISM: Artificial sequence
<220> FEATURE:
<223> OTHER INFORMATION: Arabidopsis derived ABPI endoplasmic reticulum
      targeting signal peptide

<400> SEQUENCE: 4

Met Ile Val Leu Ser Val Gly Ser Ala Ser Ser Pro Ile Val Val
1               5                   10                  15

Val Phe Ser Val Ala Leu Leu Leu Phe Tyr Phe Ser Glu Thr Ser Leu
            20                  25                  30

Gly

<210> SEQ ID NO 5
<211> LENGTH: 99
<212> TYPE: DNA
<213> ORGANISM: Artificial sequence
<220> FEATURE:
<223> OTHER INFORMATION: Coding sequence for ABPI ER target signal
      peptide

<400> SEQUENCE: 5
atgattgtgc tttctgtggg atctgcttct tcttctccaa ttgtggtggt gttctctgtg      60
gctcttcttc ttttctactt ctctgagact tctcttggc                             99

<210> SEQ ID NO 6
<211> LENGTH: 6
<212> TYPE: PRT
<213> ORGANISM: Artificial sequence
<220> FEATURE:
<223> OTHER INFORMATION: Endoplasmic reticulum retention signal peptide

<400> SEQUENCE: 6

Ser Glu Lys Asp Glu Leu
1               5

<210> SEQ ID NO 7
<211> LENGTH: 398
<212> TYPE: PRT
<213> ORGANISM: Homo sapiens
<220> FEATURE:
<221> NAME/KEY: misc_feature
<223> OTHER INFORMATION: Human mature Alpha galactosidase protein
      sequence

<400> SEQUENCE: 7

Leu Asp Asn Gly Leu Ala Arg Thr Pro Thr Met Gly Trp Leu His Trp
1               5                   10                  15

Glu Arg Phe Met Cys Asn Leu Asp Cys Gln Glu Pro Asp Ser Cys
            20                  25                  30

Ile Ser Glu Lys Leu Phe Met Glu Met Ala Glu Leu Met Val Ser Glu
        35                  40                  45

Gly Trp Lys Asp Ala Gly Tyr Glu Tyr Leu Cys Ile Asp Asp Cys Trp

```
            50                  55                  60
Met Ala Pro Gln Arg Asp Ser Glu Gly Arg Leu Gln Ala Asp Pro Gln
65                  70                  75                  80

Arg Phe Pro His Gly Ile Arg Gln Leu Ala Asn Tyr Val His Ser Lys
                85                  90                  95

Gly Leu Lys Leu Gly Ile Tyr Ala Asp Val Gly Asn Lys Thr Cys Ala
            100                 105                 110

Gly Phe Pro Gly Ser Phe Gly Tyr Tyr Asp Ile Asp Ala Gln Thr Phe
            115                 120                 125

Ala Asp Trp Gly Val Asp Leu Leu Lys Phe Asp Gly Cys Tyr Cys Asp
            130                 135                 140

Ser Leu Glu Asn Leu Ala Asp Gly Tyr Lys His Met Ser Leu Ala Leu
145                 150                 155                 160

Asn Arg Thr Gly Arg Ser Ile Val Tyr Ser Cys Glu Trp Pro Leu Tyr
                165                 170                 175

Met Trp Pro Phe Gln Lys Pro Asn Tyr Thr Glu Ile Arg Gln Tyr Cys
            180                 185                 190

Asn His Trp Arg Asn Phe Ala Asp Ile Asp Asp Ser Trp Lys Ser Ile
                195                 200                 205

Lys Ser Ile Leu Asp Trp Thr Ser Phe Asn Gln Glu Arg Ile Val Asp
            210                 215                 220

Val Ala Gly Pro Gly Gly Trp Asn Asp Pro Asp Met Leu Val Ile Gly
225                 230                 235                 240

Asn Phe Gly Leu Ser Trp Asn Gln Gln Val Thr Gln Met Ala Leu Trp
                245                 250                 255

Ala Ile Met Ala Ala Pro Leu Phe Met Ser Asn Asp Leu Arg His Ile
            260                 265                 270

Ser Pro Gln Ala Lys Ala Leu Leu Gln Asp Lys Asp Val Ile Ala Ile
            275                 280                 285

Asn Gln Asp Pro Leu Gly Lys Gln Gly Tyr Gln Leu Arg Gln Gly Asp
            290                 295                 300

Asn Phe Glu Val Trp Glu Arg Pro Leu Ser Gly Leu Ala Trp Ala Val
305                 310                 315                 320

Ala Met Ile Asn Arg Gln Glu Ile Gly Gly Pro Arg Ser Tyr Thr Ile
                325                 330                 335

Ala Val Ala Ser Leu Gly Lys Gly Val Ala Cys Asn Pro Ala Cys Phe
            340                 345                 350

Ile Thr Gln Leu Leu Pro Val Lys Arg Lys Leu Gly Phe Tyr Glu Trp
            355                 360                 365

Thr Ser Arg Leu Arg Ser His Ile Asn Pro Thr Gly Thr Val Leu Leu
            370                 375                 380

Gln Leu Glu Asn Thr Met Gln Met Ser Leu Lys Asp Leu Leu
385                 390                 395

<210> SEQ ID NO 8
<211> LENGTH: 1290
<212> TYPE: DNA
<213> ORGANISM: Artificial sequence
<220> FEATURE:
<223> OTHER INFORMATION: Coding sequence of Alpha-Galactosidase fused
      with Apple Pectinase ER signal peptide and SEKDEL

<400> SEQUENCE: 8
atggctctta agactcaatt gctctggtct ttcgttgttg tgttcgtggt ctcctttca     60 acaactagtt gctccggact tgataatgga cttgctagga ctccaactat gggatggctt   120
```

```
cattgggaac gtttcatgtg caatctcgat tgtcaagagg aaccagattc ttgcatttcc      180
gagaagcttt tcatggaaat ggctgagctt atggtttctg agggatggaa ggatgctgga      240
tatgagtacc tctgcatcga tgattgctgg atggctccac aaagagattc tgagggaagg      300
cttcaagctg atccacaaag gttcccacat ggaattaggc aactcgctaa ctacgttcac      360
tctaagggac ttaagcttgg aatctacgct gatgtggaa acaagacttg tgctggattt       420
ccaggatctt tcggttacta cgatatcgat gctcagactt tgctgattg gggagtggat       480 cttcttaagt tcgatggatg ctactgtgat tctcttgaga acctcgctga tggttataag      540
cacatgtctc tcgctcttaa tagaactgga cgttccattg tgtattcttg cgagtggcca      600
ctttacatgt ggccattcca gaagccaaac tacactgaga ttaggcaata ctgcaaccat      660
tggaggaact tcgctgatat tgatgattcc tggaagtcta tcaagtccat ccttgattgg     720
acttcattca atcaagaacg tattgtggat gttgctggac ctggtggatg gaatgatcca     780
gatatgctcg tgattgggaaa ctttggactt tcttggaacc agcaagttac tcaaatggct    840
ctctgggcta ttatggctgc tccactcttc atgtctaacg atcttaggca catttctcca      900
caagctaagg ctttgctcca ggataaggat gtgattgcta tcaaccagga tccacttgga     960
aagcaaggat accaacttag gcagggtgat aattttgagg tttgggagag gccactttct     1020
ggacttgctt gggctgttgc tatgattaac aggcaagaga ttggaggacc aaggtcttac    1080
actattgctg tggcttctct tggaaagggt gttgcttgta atccagcttg cttcattact     1140
cagcttttgc cagtgaagag gaagcttgga ttttacgagt ggacttctag gcttaggtca    1200
cacattaacc caactggaac tgtgcttctt cagctcgaga acactatgca gatgtctctt    1260
aaggatttgc tctccgagaa ggatgagctt                                      1290
```

<210> SEQ ID NO 9
<211> LENGTH: 26
<212> TYPE: PRT
<213> ORGANISM: Artificial sequence
<220> FEATURE:
<223> OTHER INFORMATION: Apple Pectinase ER targeting signal peptide
      amino acid sequence

<400> SEQUENCE: 9

Met Ala Leu Lys Thr Gln Leu Leu Trp Ser Phe Val Val Phe Val
1               5                   10                  15

Val Ser Phe Ser Thr Thr Ser Cys Ser Gly
            20                  25

<210> SEQ ID NO 10
<211> LENGTH: 78
<212> TYPE: DNA
<213> ORGANISM: Artificial sequence
<220> FEATURE:
<223> OTHER INFORMATION: Coding sequence for apple Pectinase derived ER
      targeting signal

<400> SEQUENCE: 10
atggctctta agactcaatt gctctggtct ttcgttgttg tgttcgtggt ctccttttca      60
acaactagtt gctccgga                                                    78

<210> SEQ ID NO 11
<211> LENGTH: 1296
<212> TYPE: DNA
<213> ORGANISM: Artificial sequence
<220> FEATURE:

<223> OTHER INFORMATION: Coding sequence of plant Alpha GAL fused with
     Pectinase leader peptide

<400> SEQUENCE: 11

```
atggctctta agactcaatt gctctggtct ttcgttgttg tgttcgtggt ctccttttca    60
acaactagtt gctccggaga attccttgat aatggattgg ccaggacacc aactatggga   120
tggctgcatt gggagcgttt tatgtgtaac cttgactgcc aagaagagcc tgattcttgc   180
atctcagaga agctctttat ggaaatggct gagctgatgg tttctgaagg ctggaaagac   240
gcaggttatg agtatttgtg catcgacgat tgctggatgg ctccacagag agatagtgaa   300
gggagacttc aagcagatcc tcagaggttt ccacatggta ttagacagct cgccaattat   360
gttcactcca agggccttaa gttggggata tacgctgatg tgggaaacaa acctgtgct   420
ggatttcctg gttccttcgg ctattacgat attgacgcac aaacctttgc tgattgggga   480
gttgacctcc ttaaattcga tggctgttac tgtgattcac ttgagaatct cgccgacggt   540
tataagcaca tgtctctcgc tttgaacagg actggaagga gcatagtcta ctcctgtgaa   600
tggccacttt acatgtggcc tttccagaag ccaaactaca ctgagattag cagtattgc   660
aaccactggc gtaattttgc cgatatcgac gattcttgga gtccatcaa gagcattctg   720
gattggacat ccttcaatca ggaaaggatt gtggatgttg ctggacctgg tggatggaat   780
gatcctgaca tgttggtgat agggaacttt ggtctctcat ggaatcagca agttacccaa   840
atggcactct gggctattat ggctgcacca ctcttcatgt ctaacgacct caggcatatc   900
tcacctcaag caaaggcatt gctgcaagac aaagacgtca ttgccattaa ccaggaccct   960
cttgggaagc aaggttatca acttcgtcaa ggcgataact ttgaagtgtg ggagagacca  1020
ttgtctggac ttgcttgggc tgttgccatg attaataggc aagaaatcgg tggcccaaga  1080
agttatacaa tcgctgttgc aagtcttgga aaaggtgtcg cttgtaatcc tgcctgtttc  1140
attactcagc tcctgcctgt gaaaagaaag ttggggttct atgaatggac ttcaagactc  1200
aggagccata ttaaccctac cggaacagtt cttctccaac tggagaacac catgcaaatg  1260
tccctcaaag atcttagtga aggacgag ctctga                              1296
```

<210> SEQ ID NO 12
<211> LENGTH: 431
<212> TYPE: PRT
<213> ORGANISM: Artificial sequence
<220> FEATURE:
<223> OTHER INFORMATION: Plant Alpha GAL fused with Pectinase leader
      peptide, amino acid sequence

<400> SEQUENCE: 12

```
Met Ala Leu Lys Thr Gln Leu Leu Trp Ser Phe Val Val Phe Val
1               5                   10                  15

Val Ser Phe Ser Thr Thr Ser Cys Ser Gly Glu Phe Leu Asp Asn Gly
                20                  25                  30

Leu Ala Arg Thr Pro Thr Met Gly Trp Leu His Trp Glu Arg Phe Met
        35                  40                  45

Cys Asn Leu Asp Cys Gln Glu Glu Pro Asp Ser Cys Ile Ser Glu Lys
    50                  55                  60

Leu Phe Met Glu Met Ala Glu Leu Met Val Ser Glu Gly Trp Lys Asp
65                  70                  75                  80

Ala Gly Tyr Glu Tyr Leu Cys Ile Asp Asp Cys Trp Met Ala Pro Gln
                85                  90                  95

Arg Asp Ser Glu Gly Arg Leu Gln Ala Asp Pro Gln Arg Phe Pro His
```

|   |   |   | 100 |   |   |   | 105 |   |   |   | 110 |   |
|---|---|---|---|---|---|---|---|---|---|---|---|---|

Gly Ile Arg Gln Leu Ala Asn Tyr Val His Ser Lys Gly Leu Lys Leu
            115             120            125

Gly Ile Tyr Ala Asp Val Gly Asn Lys Thr Cys Ala Gly Phe Pro Gly
130             135            140

Ser Phe Gly Tyr Tyr Asp Ile Asp Ala Gln Thr Phe Ala Asp Trp Gly
145             150            155            160

Val Asp Leu Leu Lys Phe Asp Gly Cys Tyr Cys Asp Ser Leu Glu Asn
            165           170            175

Leu Ala Asp Gly Tyr Lys His Met Ser Leu Ala Leu Asn Arg Thr Gly
            180           185           190

Arg Ser Ile Val Tyr Ser Cys Glu Trp Pro Leu Tyr Met Trp Pro Phe
            195           200           205

Gln Lys Pro Asn Tyr Thr Glu Ile Arg Gln Tyr Cys Asn His Trp Arg
            210           215           220

Asn Phe Ala Asp Ile Asp Asp Ser Trp Lys Ser Ile Lys Ser Ile Leu
225             230            235            240

Asp Trp Thr Ser Phe Asn Gln Glu Arg Ile Val Asp Val Ala Gly Pro
            245           250           255

Gly Gly Trp Asn Asp Pro Asp Met Leu Val Ile Gly Asn Phe Gly Leu
            260           265           270

Ser Trp Asn Gln Gln Val Thr Gln Met Ala Leu Trp Ala Ile Met Ala
            275           280           285

Ala Pro Leu Phe Met Ser Asn Asp Leu Arg His Ile Ser Pro Gln Ala
            290           295           300

Lys Ala Leu Leu Gln Asp Lys Asp Val Ile Ala Ile Asn Gln Asp Pro
305             310            315            320

Leu Gly Lys Gln Gly Tyr Gln Leu Arg Gln Gly Asp Asn Phe Glu Val
            325           330           335

Trp Glu Arg Pro Leu Ser Gly Leu Ala Trp Ala Val Ala Met Ile Asn
            340           345           350

Arg Gln Glu Ile Gly Gly Pro Arg Ser Tyr Thr Ile Ala Val Ala Ser
            355           360           365

Leu Gly Lys Gly Val Ala Cys Asn Pro Ala Cys Phe Ile Thr Gln Leu
            370           375           380

Leu Pro Val Lys Arg Lys Leu Gly Phe Tyr Glu Trp Thr Ser Arg Leu
385             390            395            400

Arg Ser His Ile Asn Pro Thr Gly Thr Val Leu Leu Gln Leu Glu Asn
            405           410           415

Thr Met Gln Met Ser Leu Lys Asp Leu Ser Glu Lys Asp Glu Leu
            420           425           430

<210> SEQ ID NO 13
<211> LENGTH: 1278
<212> TYPE: DNA
<213> ORGANISM: Artificial sequence
<220> FEATURE:
<223> OTHER INFORMATION: Optimized coding sequence of plant derived
    Alpha GAL II and Chitinase signal peptide fusion protein

<400> SEQUENCE: 13
atgaagacta atcttttttct ctttctcatc ttttcacttc tcctatcatt atcctcggcc    60
gaattccttg ataatggact tgctaggact ccaactatgg gatggcttca ttgggaacgt   120
ttcatgtgca atctcgattg tcaagaggaa ccagattctt gcatttccga gaagcttttc   180

```
atggaaatgg ctgagcttat ggtttctgag ggatggaagg atgctggata tgagtacctc    240
tgcatcgatg attgctggat ggctccacaa agagattctg agggaaggct tcaagctgat    300
ccacaaaggt tcccacatgg aattaggcaa ctcgctaact acgttcactc taagggactt    360
aagcttggaa tctacgctga tgtgggaaac aagacttgtg ctggatttcc aggatctttc    420
ggttactacg atatcgatgc tcagacttt gctgattggg gagtggatct tcttaagttc    480
gatggatgct actgtgattc tcttgagaac ctcgctgatg gttataagca catgtctctc    540
gctcttaata gaactggacg ttccattgtg tattcttgcg agtggccact ttacatgtgg    600
ccattccaga agccaaacta cactgagatt aggcaatact gcaaccattg gaggaacttc    660
gctgatattg atgattcctg gaagtctatc aagtccatcc ttgattggac ttcattcaat    720
caagaacgta ttgtggatgt tgctggacct ggtggatgga atgatccaga tatgctcgtg    780 attggaaaact ttggactttc ttggaaccag caagttactc aaatggctct ctgggctatt    840
atggctgctc cactcttcat gtctaacgat cttaggcaca tttctccaca agctaaggct    900
ttgctccagg ataaggatgt gattgctatc aaccaggatc cacttggaaa gcaaggatac    960
caacttaggc agggtgataa ttttgaggtt tgggagaggc cactttctgg acttgcttgg   1020
gctgttgcta tgattaacag caagagatt ggaggaccaa ggtcttacac tattgctgtg   1080
gcttctcttg aaagggtgt tgcttgtaat ccagcttgct tcattactca gcttttgcca   1140
gtgaagagga agcttggatt ttacgagtgg acttctaggc ttaggtcaca cattaaccca   1200
actggaactg tgcttcttca gctcgagaac actatgcaga tgtctcttaa ggatttgctc   1260
tccgagaagg atgagctt                                                  1278
```

<210> SEQ ID NO 14
<211> LENGTH: 22
<212> TYPE: PRT
<213> ORGANISM: Artificial sequence
<220> FEATURE:
<223> OTHER INFORMATION: Basic endochitinase B ER targeting signal
      peptide amino acid sequence

<400> SEQUENCE: 14

Met Lys Thr Asn Leu Phe Leu Phe Leu Ile Phe Ser Leu Leu Leu Ser
1               5                   10                  15
Leu Ser Ser Ala Glu Phe
            20

<210> SEQ ID NO 15
<211> LENGTH: 66
<212> TYPE: DNA
<213> ORGANISM: Artificial sequence
<220> FEATURE:
<223> OTHER INFORMATION: Basic endochitinase B ER targeting signal
      peptide coding sequence

<400> SEQUENCE: 15
atgaagacta atcttttct ctttctcatc ttttcacttc tcctatcatt atcctcggcc    60
gaattc                                                              66

<210> SEQ ID NO 16
<211> LENGTH: 399
<212> TYPE: PRT
<213> ORGANISM: Artificial sequence
<220> FEATURE:
<223> OTHER INFORMATION: Recombinant mature Alpah-Gal protein sequence
      with N' terminal G

<400> SEQUENCE: 16

```
Gly Leu Asp Asn Gly Leu Ala Arg Thr Pro Thr Met Gly Trp Leu His
1               5                   10                  15

Trp Glu Arg Phe Met Cys Asn Leu Asp Cys Gln Glu Pro Asp Ser
            20                  25                  30

Cys Ile Ser Glu Lys Leu Phe Met Glu Met Ala Glu Leu Met Val Ser
        35                  40                  45

Glu Gly Trp Lys Asp Ala Gly Tyr Glu Tyr Leu Cys Ile Asp Asp Cys
    50                  55                  60

Trp Met Ala Pro Gln Arg Asp Ser Glu Gly Arg Leu Gln Ala Asp Pro
65                  70                  75                  80

Gln Arg Phe Pro His Gly Ile Arg Gln Leu Ala Asn Tyr Val His Ser
                85                  90                  95

Lys Gly Leu Lys Leu Gly Ile Tyr Ala Asp Val Gly Asn Lys Thr Cys
            100                 105                 110

Ala Gly Phe Pro Gly Ser Phe Gly Tyr Tyr Asp Ile Asp Ala Gln Thr
        115                 120                 125

Phe Ala Asp Trp Gly Val Asp Leu Leu Lys Phe Asp Gly Cys Tyr Cys
130                 135                 140

Asp Ser Leu Glu Asn Leu Ala Asp Gly Tyr Lys His Met Ser Leu Ala
145                 150                 155                 160

Leu Asn Arg Thr Gly Arg Ser Ile Val Tyr Ser Cys Glu Trp Pro Leu
                165                 170                 175

Tyr Met Trp Pro Phe Gln Lys Pro Asn Tyr Thr Glu Ile Arg Gln Tyr
            180                 185                 190

Cys Asn His Trp Arg Asn Phe Ala Asp Ile Asp Asp Ser Trp Lys Ser
        195                 200                 205

Ile Lys Ser Ile Leu Asp Trp Thr Ser Phe Asn Gln Glu Arg Ile Val
210                 215                 220

Asp Val Ala Gly Pro Gly Gly Trp Asn Asp Pro Asp Met Leu Val Ile
225                 230                 235                 240

Gly Asn Phe Gly Leu Ser Trp Asn Gln Gln Val Thr Gln Met Ala Leu
                245                 250                 255

Trp Ala Ile Met Ala Ala Pro Leu Phe Met Ser Asn Asp Leu Arg His
            260                 265                 270

Ile Ser Pro Gln Ala Lys Ala Leu Leu Gln Asp Lys Asp Val Ile Ala
        275                 280                 285

Ile Asn Gln Asp Pro Leu Gly Lys Gln Gly Tyr Gln Leu Arg Gln Gly
290                 295                 300

Asp Asn Phe Glu Val Trp Glu Arg Pro Leu Ser Gly Leu Ala Trp Ala
305                 310                 315                 320

Val Ala Met Ile Asn Arg Gln Glu Ile Gly Gly Pro Arg Ser Tyr Thr
                325                 330                 335

Ile Ala Val Ala Ser Leu Gly Lys Gly Val Ala Cys Asn Pro Ala Cys
            340                 345                 350

Phe Ile Thr Gln Leu Leu Pro Val Lys Arg Lys Leu Gly Phe Tyr Glu
        355                 360                 365

Trp Thr Ser Arg Leu Arg Ser His Ile Asn Pro Thr Gly Thr Val Leu
370                 375                 380

Leu Gln Leu Glu Asn Thr Met Gln Met Ser Leu Lys Asp Leu Leu
385                 390                 395
```

<210> SEQ ID NO 17

```
<211> LENGTH: 4
<212> TYPE: PRT
<213> ORGANISM: Artificial sequence
<220> FEATURE:
<223> OTHER INFORMATION: Endoplasmic reticulum retention signal peptide

<400> SEQUENCE: 17

Lys Asp Glu Leu
1

<210> SEQ ID NO 18
<211> LENGTH: 1194
<212> TYPE: DNA
<213> ORGANISM: Artificial sequence
<220> FEATURE:
<223> OTHER INFORMATION: Optimized coding sequence for mature Alpah-Gal
      without ABPI or SEKDEL signal peptides

<400> SEQUENCE: 18
cttgataatg gacttgctag gactccaact atgggatggc ttcattggga acgtttcatg      60
tgcaatctcg attgtcaaga ggaaccagat tcttgcattt ccgagaagct tttcatggaa     120
atggctgagc ttatggtttc tgagggatgg aaggatgctg gatatgagta cctctgcatc     180
gatgattgct ggatggctcc acaaagagat tctgagggaa ggcttcaagc tgatccacaa     240
aggttcccac atggaattag gcaactcgct aactacgttc actctaaggg acttaagctt     300
ggaatctacg ctgatgtggg aaacaagact tgtgctggat tccaggatc tttcggttac     360 tacgatatcg atgctcagac ttttgctgat tggggagtgg atcttcttaa gttcgatgga     420
tgctactgtg attctcttga gaacctcgct gatggttata agcacatgtc tctcgctctt     480
aatagaactg gacgttccat tgtgtattct tgcgagtggc cactttacat gtggccattc     540
cagaagccaa actacactga gattaggcaa tactgcaacc attggaggaa cttcgctgat     600
attgatgatt cctggaagtc tatcaagtcc atccttgatt ggacttcatt caatcaagaa     660
cgtattgtgg atgttgctgg acctggtgga tggaatgatc cagatatgct cgtgattgga     720
aactttggac tttcttggaa ccagcaagtt actcaaatgg ctctctgggc tattatggct     780
gctccactct tcatgtctaa cgatcttagg cacatttctc cacaagctaa ggctttgctc     840
caggataagg atgtgattgc tatcaaccag gatccacttg gaaagcaagg ataccaactt     900
aggcagggtg ataattttga ggtttgggag aggccacttt ctggacttgc ttgggctgtt     960
gctatgatta caggcaaga gattggagga ccaaggtctt acactattgc tgtggcttct    1020
cttggaaagg gtgttgcttg taatccagct tgcttcatta ctcagctttt gccagtgaag    1080
aggaagcttg gattttacga gtggacttct aggcttaggt cacacattaa cccaactgga    1140
actgtgcttc ttcagctcga gaacactatg cagatgtctc ttaaggattt gctc         1194

<210> SEQ ID NO 19
<211> LENGTH: 18
<212> TYPE: DNA
<213> ORGANISM: Artificial sequence
<220> FEATURE:
<223> OTHER INFORMATION: Coding sequence for SEKDEL  ER retention signal

<400> SEQUENCE: 19
tccgagaagg atgagctt                                                    18

<210> SEQ ID NO 20
<211> LENGTH: 404
<212> TYPE: PRT
<213> ORGANISM: Artificial sequence
```

-continued

```
<220> FEATURE:
<223> OTHER INFORMATION: Recombinant A-Gal mature protein fused to
      SEKDEL without N' terminal G

<400> SEQUENCE: 20
```

| | | | | | | | | | | | | | |
|---|---|---|---|---|---|---|---|---|---|---|---|---|---|
| Leu | Asp | Asn | Gly | Leu | Ala | Arg | Thr | Pro | Thr | Met | Gly | Trp | Leu | His | Trp |
| 1 | | | | 5 | | | | | 10 | | | | | 15 | |

Leu Asp Asn Gly Leu Ala Arg Thr Pro Thr Met Gly Trp Leu His Trp
1               5                   10                  15

Glu Arg Phe Met Cys Asn Leu Asp Cys Gln Glu Pro Asp Ser Cys
            20                  25                  30

Ile Ser Glu Lys Leu Phe Met Glu Met Ala Glu Leu Met Val Ser Glu
                35                  40                  45

Gly Trp Lys Asp Ala Gly Tyr Glu Tyr Leu Cys Ile Asp Asp Cys Trp
50                  55                  60

Met Ala Pro Gln Arg Asp Ser Glu Gly Arg Leu Gln Ala Asp Pro Gln
65                  70                  75                  80

Arg Phe Pro His Gly Ile Arg Gln Leu Ala Asn Tyr Val His Ser Lys
                85                  90                  95

Gly Leu Lys Leu Gly Ile Tyr Ala Asp Val Gly Asn Lys Thr Cys Ala
                100                 105                 110

Gly Phe Pro Gly Ser Phe Gly Tyr Tyr Asp Ile Asp Ala Gln Thr Phe
            115                 120                 125

Ala Asp Trp Gly Val Asp Leu Leu Lys Phe Asp Gly Cys Tyr Cys Asp
130                 135                 140

Ser Leu Glu Asn Leu Ala Asp Gly Tyr Lys His Met Ser Leu Ala Leu
145                 150                 155                 160

Asn Arg Thr Gly Arg Ser Ile Val Tyr Ser Cys Glu Trp Pro Leu Tyr
                165                 170                 175

Met Trp Pro Phe Gln Lys Pro Asn Tyr Thr Glu Ile Arg Gln Tyr Cys
            180                 185                 190

Asn His Trp Arg Asn Phe Ala Asp Ile Asp Asp Ser Trp Lys Ser Ile
        195                 200                 205

Lys Ser Ile Leu Asp Trp Thr Ser Phe Asn Gln Glu Arg Ile Val Asp
210                 215                 220

Val Ala Gly Pro Gly Gly Trp Asn Asp Pro Asp Met Leu Val Ile Gly
225                 230                 235                 240

Asn Phe Gly Leu Ser Trp Asn Gln Gln Val Thr Gln Met Ala Leu Trp
                245                 250                 255

Ala Ile Met Ala Ala Pro Leu Phe Met Ser Asn Asp Leu Arg His Ile
                260                 265                 270

Ser Pro Gln Ala Lys Ala Leu Leu Gln Asp Lys Asp Val Ile Ala Ile
            275                 280                 285

Asn Gln Asp Pro Leu Gly Lys Gln Gly Tyr Gln Leu Arg Gln Gly Asp
290                 295                 300

Asn Phe Glu Val Trp Glu Arg Pro Leu Ser Gly Leu Ala Trp Ala Val
305                 310                 315                 320

Ala Met Ile Asn Arg Gln Glu Ile Gly Gly Pro Arg Ser Tyr Thr Ile
                325                 330                 335

Ala Val Ala Ser Leu Gly Lys Gly Val Ala Cys Asn Pro Ala Cys Phe
            340                 345                 350

Ile Thr Gln Leu Leu Pro Val Lys Arg Lys Leu Gly Phe Tyr Glu Trp
            355                 360                 365

Thr Ser Arg Leu Arg Ser His Ile Asn Pro Thr Gly Thr Val Leu Leu
370                 375                 380

Gln Leu Glu Asn Thr Met Gln Met Ser Leu Lys Asp Leu Leu Ser Glu

<210> SEQ ID NO 21
<211> LENGTH: 405
<212> TYPE: PRT
<213> ORGANISM: Artificial sequence
<220> FEATURE:
<223> OTHER INFORMATION: Recombinant A-Gal mature protein with N' terminal G and fused to SEKDEL

<400> SEQUENCE: 21

```
Gly Leu Asp Asn Gly Leu Ala Arg Thr Pro Thr Met Gly Trp Leu His
1               5                   10                  15

Trp Glu Arg Phe Met Cys Asn Leu Asp Cys Gln Glu Glu Pro Asp Ser
            20                  25                  30

Cys Ile Ser Glu Lys Leu Phe Met Glu Met Ala Glu Leu Met Val Ser
        35                  40                  45

Glu Gly Trp Lys Asp Ala Gly Tyr Glu Tyr Leu Cys Ile Asp Asp Cys
    50                  55                  60

Trp Met Ala Pro Gln Arg Asp Ser Glu Gly Arg Leu Gln Ala Asp Pro
65                  70                  75                  80

Gln Arg Phe Pro His Gly Ile Arg Gln Leu Ala Asn Tyr Val His Ser
                85                  90                  95

Lys Gly Leu Lys Leu Gly Ile Tyr Ala Asp Val Gly Asn Lys Thr Cys
            100                 105                 110

Ala Gly Phe Pro Gly Ser Phe Gly Tyr Tyr Asp Ile Asp Ala Gln Thr
        115                 120                 125

Phe Ala Asp Trp Gly Val Asp Leu Leu Lys Phe Asp Gly Cys Tyr Cys
    130                 135                 140

Asp Ser Leu Glu Asn Leu Ala Asp Gly Tyr Lys His Met Ser Leu Ala
145                 150                 155                 160

Leu Asn Arg Thr Gly Arg Ser Ile Val Tyr Ser Cys Glu Trp Pro Leu
                165                 170                 175

Tyr Met Trp Pro Phe Gln Lys Pro Asn Tyr Thr Glu Ile Arg Gln Tyr
            180                 185                 190

Cys Asn His Trp Arg Asn Phe Ala Asp Ile Asp Asp Ser Trp Lys Ser
        195                 200                 205

Ile Lys Ser Ile Leu Asp Trp Thr Ser Phe Asn Gln Glu Arg Ile Val
    210                 215                 220

Asp Val Ala Gly Pro Gly Gly Trp Asn Asp Pro Asp Met Leu Val Ile
225                 230                 235                 240

Gly Asn Phe Gly Leu Ser Trp Asn Gln Gln Val Thr Gln Met Ala Leu
                245                 250                 255

Trp Ala Ile Met Ala Ala Pro Leu Phe Met Ser Asn Asp Leu Arg His
            260                 265                 270

Ile Ser Pro Gln Ala Lys Ala Leu Leu Gln Asp Lys Asp Val Ile Ala
        275                 280                 285

Ile Asn Gln Asp Pro Leu Gly Lys Gln Gly Tyr Gln Leu Arg Gln Gly
    290                 295                 300

Asp Asn Phe Glu Val Trp Glu Arg Pro Leu Ser Gly Leu Ala Trp Ala
305                 310                 315                 320

Val Ala Met Ile Asn Arg Gln Glu Ile Gly Gly Pro Arg Ser Tyr Thr
                325                 330                 335

Ile Ala Val Ala Ser Leu Gly Lys Gly Val Ala Cys Asn Pro Ala Cys
```

|  | 340 |  | 345 |  | 350 |  |
|---|---|---|---|---|---|---|
| Phe Ile Thr Gln Leu Leu Pro Val Lys Arg Lys Leu Gly Phe Tyr Glu |

|  | 355 |  | 360 |  | 365 |  |
|---|---|---|---|---|---|---|
| Trp Thr Ser Arg Leu Arg Ser His Ile Asn Pro Thr Gly Thr Val Leu |

|  | 370 |  | 375 |  | 380 |  |
|---|---|---|---|---|---|---|
| Leu Gln Leu Glu Asn Thr Met Gln Met Ser Leu Lys Asp Leu Leu Ser |
| 385 |  |  | 390 |  | 395 |  | 400 |

Glu Lys Asp Glu Leu
          405

<210> SEQ ID NO 22
<211> LENGTH: 1212
<212> TYPE: DNA
<213> ORGANISM: Artificial sequence
<220> FEATURE:
<223> OTHER INFORMATION: Optimized coding sequence for mature A-Gal
      protein fused to SEKDEL without ABPI

<400> SEQUENCE: 22

```
cttgataatg gacttgctag gactccaact atgggatggc ttcattggga acgtttcatg      60
tgcaatctcg attgtcaaga ggaaccagat tcttgcattt ccgagaagct tttcatggaa     120
atggctgagc ttatggtttc tgagggatgg aaggatgctg atatgagta cctctgcatc      180
gatgattgct ggatggctcc acaaagagat tctgagggaa ggcttcaagc tgatccacaa     240
aggttcccac atgaattag gcaactcgct aactacgttc actctaaggg acttaagctt      300
ggaatctacg ctgatgtggg aaacaagact tgtgctggat ttccaggatc tttcggttac     360
tacgatatcg atgctcagac ttttgctgat tggggagtgg atcttcttaa gttcgatgga     420
tgctactgtg attctcttga acctcgctg atggttata agcacatgtc tctcgctctt       480
aatagaactg gacgttccat tgtgtattct tgcgagtggc actttacat gtggccattc      540
cagaagccaa actacactga gattaggcaa tactgcaacc attggaggaa cttcgctgat     600
attgatgatt cctggaagtc tatcaagtcc atccttgatt ggacttcatt caatcaagaa     660
cgtattgtgg atgttgctgg acctggtgga tggaatgatc cagatatgct cgtgattgga     720
aactttggac tttcttggaa ccagcaagtt actcaaatgg ctctctgggc tattatggct     780
gctccactct tcatgtctaa cgatcttagg cacatttctc cacaagctaa ggctttgctc     840
caggataagg atgtgattgc tatcaaccag gatccacttg aaagcaagg ataccaactt      900
aggcagggtg taaattttga ggtttgggag aggccacttt ctggacttgc ttgggctgtt     960
gctatgatta caggcaaga gattggagga ccaaggtctt acactattgc tgtggcttct    1020
cttggaaagg gtgttgcttg taatccagct tgcttcatta ctcagctttt gccagtgaag    1080
aggaagcttg gattttacga gtggacttct aggcttaggt cacacattaa cccaactgga    1140
actgtgcttc ttcagctcga gaacactatg cagatgtctc ttaaggattt gctctccgag    1200
aaggatgagc tt                                                        1212
```

<210> SEQ ID NO 23
<211> LENGTH: 1215
<212> TYPE: DNA
<213> ORGANISM: Artificial sequence
<220> FEATURE:
<223> OTHER INFORMATION: Optimized coding sequence for mature A-Gal
      protein with N' terminal G and SEKDEL

<400> SEQUENCE: 23

```
ggccttgata atggacttgc taggactcca actatgggat ggcttcattg ggaacgtttc      60
```

```
atgtgcaatc tcgattgtca agaggaacca gattcttgca tttccgagaa gcttttcatg    120
gaaatggctg agcttatggt ttctgaggga tggaaggatg ctggatatga gtacctctgc    180
atcgatgatt gctggatggc tccacaaaga gattctgagg gaaggcttca agctgatcca    240
caaaggttcc cacatggaat taggcaactc gctaactacg ttcactctaa gggacttaag    300
cttggaatct acgctgatgt gggaaacaag acttgtgctg gatttccagg atctttcggt    360
tactacgata tcgatgctca gacttttgct gattggggag tggatcttct taagttcgat    420
ggatgctact gtgattctct tgagaacctc gctgatggtt ataagcacat gtctctcgct    480
cttaatagaa ctggacgttc cattgtgtat tcttgcgagt ggccacttta catgtggcca    540
ttccagaagc caaactacac tgagattagg caatactgca accattggag gaacttcgct    600
gatattgatg attcctggaa gtctatcaag tccatccttg attggacttc attcaatcaa    660
gaacgtattg tggatgttgc tggacctggt ggatggaatg atccagatat gctcgtgatt    720
ggaaactttg gactttcttg gaaccagcaa gttactcaaa tggctctctg ggctattatg    780
gctgctccac tcttcatgtc taacgatctt aggcacattt ctccacaagc taaggctttg    840
ctccaggata aggatgtgat tgctatcaac caggatccac ttggaaagca aggataccaa    900
cttaggcagg gtgataattt tgaggtttgg gagaggccac tttctggact tgcttgggct    960
gttgctatga ttaacaggca agagattgga ggaccaaggt cttacactat tgctgtggct    1020
tctcttggaa agggtgttgc ttgtaatcca gcttgcttca ttactcagct tttgccagtg    1080
aagaggaagc ttggatttta cgagtggact tctaggctta ggtcacacat taacccaact    1140
ggaactgtgc ttcttcagct cgagaacact atgcagatgt ctcttaagga tttgctctcc    1200
gagaaggatg agctt                                                     1215
```